US010968484B2

(12) United States Patent
Johannessen et al.

(10) Patent No.: US 10,968,484 B2
(45) Date of Patent: Apr. 6, 2021

(54) METHODS OF IDENTIFYING RESPONSES TO MAP KINASE INHIBITION THERAPY

(71) Applicants: The Broad Institute, Inc., Cambridge, MA (US); Dana-Farber Cancer Institute, Inc., Boston, MA (US)

(72) Inventors: Cory M. Johannessen, Roslindale, MA (US); David J. Konieczkowski, Brookline, MA (US); Levi A. Garraway, Newton, MA (US)

(73) Assignees: The Broad Institute, Inc., Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 421 days.

(21) Appl. No.: 14/774,909

(22) PCT Filed: Mar. 12, 2014

(86) PCT No.: PCT/US2014/023927
§ 371 (c)(1),
(2) Date: Sep. 11, 2015

(87) PCT Pub. No.: WO2014/150671
PCT Pub. Date: Sep. 25, 2014

(65) Prior Publication Data
US 2016/0024589 A1    Jan. 28, 2016

Related U.S. Application Data

(60) Provisional application No. 61/800,304, filed on Mar. 15, 2013.

(51) Int. Cl.
*C12Q 1/68*    (2018.01)
*C12Q 1/6886*    (2018.01)
*G01N 33/574*    (2006.01)
*A61K 31/437*    (2006.01)

(52) U.S. Cl.
CPC .......... *C12Q 1/6886* (2013.01); *A61K 31/437* (2013.01); *G01N 33/5743* (2013.01); *G01N 33/57484* (2013.01); *C12Q 2600/106* (2013.01); *C12Q 2600/158* (2013.01); *G01N 2500/10* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,856,094 A | 1/1999 | Sidransky et al. |
| 5,989,885 A | 11/1999 | Teng et al. |
| 2008/0131885 A1 | 6/2008 | Pratilas et al. |
| 2009/0023149 A1 | 1/2009 | Knudsen |
| 2010/0130527 A1 | 5/2010 | Lehrer et al. |
| 2013/0059851 A1 | 3/2013 | Garraway et al. |
| 2015/0141470 A1 | 5/2015 | Garraway et al. |

FOREIGN PATENT DOCUMENTS

| | | |
|---|---|---|
| WO | WO 2005/118865 A2 | 12/2005 |
| WO | WO 2011/112678 A1 | 9/2011 |
| WO | WO 2014/150671 A1 | 9/2014 |

OTHER PUBLICATIONS

Handbook of Chemistry and Physics, 49th Edition, 1968, Weast (ed.), the Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Ahn et al., A dominant-negative inhibitor of CREB reveals that it is a general mediator of stimulus-dependent transcription of c-fos. Mol Cell Biol. Feb. 1998;18(2):967-77.
Alvarez et al., The Axl receptor tyrosine kinase is an adverse prognostic factor and a therapeutic target in esophageal adenocarcinoma. Cancer Biol Ther. Nov. 15, 2010;10(10):1009-18. doi: 10.4161/cbt.10.10.13248. Epub Nov. 15, 2010.
Aronov et al., Structure-guided design of potent and selective pyrimidylpyrrole inhibitors of extracellular signal-regulated kinase (ERK) using conformational control. J Med Chem. Oct. 22, 2009;52(20):6362-8. doi: 10.1021/jm900630q.—Abstract Only.
Benner et al., Evolution, language and analogy in functional genomics. Trends Genet. Jul. 2001;17(7):414-8.
Chabert et al., Cell culture of tumors alters endogenous poly(ADPR)polymerase expression and activity. Int J Cancer. Mar. 12, 1993;53(5):837-42.
Chapman et al., Improved survival with vemurafenib in melanoma with BRAF V600E mutation. N Engl J Med. Jun. 30, 2011;364(26):2507-16. doi: 10.1056/NEJMoa1103782. Epub Jun. 5, 2011.
Cheung et al., Natural variation in human gene expression assessed in lymphoblastoid cells. Nat Genet. Mar. 2003;33(3):422-5. Epub Feb. 3, 2003.
Corcoran et al., BRAF gene amplification can promote acquired resistance to MEK inhibitors in cancer cells harboring the BRAF V600E mutation. Sci Signal. Nov. 23, 2010;3(149):ra84. doi: 10.1126/scisignal.2001148.
Crews et al., The primary structure of MEK, a protein kinase that phosphorylates the ERK gene product. Science. Oct. 16, 1992;258(5081):478-80.—Abstract Only.
Davies et al., Mutations of the BRAF gene in human cancer. Nature. Jun. 27, 2002;417(6892):949-54. Epub Jun. 9, 2002.
Davis et al., Oncogenic MITF dysregulation in clear cell sarcoma: defining the MiT family of human cancers. Cancer Cell. Jun. 2006;9(6):473-84.
Dermer, Another Anniversary for the War on Cancer. Bio/Technology. 1994;12:320.

(Continued)

*Primary Examiner* — James Martinell
(74) *Attorney, Agent, or Firm* — Wolf, Greenfield & Sacks, P.C.

(57) ABSTRACT

The invention provides methods and devices for determining molecular signatures in a cancer that predict response to a MARPK pathway inhibitor and methods of use of such signatures.

23 Claims, 1 Drawing Sheet

(56) References Cited

OTHER PUBLICATIONS

Dumaz et al., RAS mutations are accompanied by switching signaling from BRAF to CRAF and disrupted cyclic AMP signaling. Cancer Res. Oct. 1, 2006;66(19):9483-91.

Eastham et al., Relationships between clonogenic cell survival, DNA damage and chromosomal radiosensitivity in nine human cervix carcinoma cell lines. Int J Radial Biol. Mar. 2001;77(3):295-302.

Emery et al., MEK1 mutations confer resistance to MEK and B-RAF inhibition. Proc Natl Acad Sci USA. Dec. 1, 2009;106(48):20411-6. doi: 10.1073/pnas.0905833106. Epub Nov. 13, 2009.

Flaherty et al., Combined BRAF and MEK inhibition in melanoma with BRAF V600 mutations. N Engl J Med. Nov. 2012;367(18):1694-703. doi: 10.1056/NEJMoa1210093. Epub Sep. 29, 2012.

Flaherty et al., Improved survival with MEK inhibition in BRAF-mutated melanoma. N Engl J Med. Jul. 12, 2012;367(2):107-14. doi: 10.1056/NEJMoa1203421. Epub Jun. 4, 2012.

Flaherty et al., Inhibition of mutated, activated BRAF in metastatic melanoma. N Engl J Med. Aug. 26, 2010;363(9):809-19. doi: 10.1056/NEJMoa1002011.

Garraway et al., Integrative genomic analyses identify MITF as a lineage survival oncogene amplified in malignant melanoma. Nature. Jul. 7, 2005;436(7047):117-22.

Greenbaum et al., Comparing protein abundance and mRNA expression levels on a genomic scale. Genome Biol. 2003;4(9):117. Epub Aug. 29, 2003.

Hauschild et al., Multicenter phase II trial of the histone deacetylase inhibitor pyridylmethyl-N-{4-[(2-aminophenyl)-carbamoyl]-benzyl}-carbamate in pretreated metastatic melanoma. Melanoma Res. Aug. 2008;18(4):274-8. doi: 10.1097/CMR.0b013e328307c248.

Hayward, Genetics of melanoma predisposition. Oncogene. May 19, 2003;22(20):3053-62.

Hemesath et al., MAP kinase links the transcription factor Microphthalmia to c-Kit signalling in melanocytes. Nature. Jan. 15, 1998;391(6664):298-301.—Abstract Only.

Hernández et al., Novel inhibitors of Rac1 in metastatic breast cancer. P R Health Sci J. Dec. 2010;29(4):348-56.

Hodgkinson et al., Mutations at the mouse microphthalmia locus are associated with defects in a gene encoding a novel basic-helix-loop-helix-zipper protein. Cell. Jul. 30, 1993;74(2):395-404.—Abstract Only.

Hoeflich et al., Antitumor efficacy of the novel RAF inhibitor GDC-0879 is predicted by BRAFV600E mutational status and sustained extracellular signal-regulated kinase/mitogen-activated protein kinase pathway suppression. Cancer Res. Apr. 1, 2009;69(7):3042-51. doi: 10.1158/0008-5472.CAN-08-3563. Epub Mar. 10, 2009.

Huber et al., A tissue-restricted cAMP transcriptional response: SOX10 modulates alpha-melanocyte-stimulating hormone-triggered expression of microphthalmia-associated transcription factor in melanocytes. J Biol Chem. Nov. 14, 2003;278(46):45224-30. Epub Aug. 27, 2003.

Ikawa et al., B-raf, a new member of the raf family, is activated by DNA rearrangement. Mol Cell Biol. Jun. 1988;8(6):2651-4.

Infante et al., Safety and efficacy results from the first-in-human study of the oral MEK 1/2 inhibitor GSK1120212. Journal of Clinical Oncology, 2010 ASCO Annual Meeting Abstracts. May 2010;28(15 Suppl) Abstract No. 2503.

Jané-Valbuena et al., An oncogenic role for ETV1 in melanoma. Cancer Res. Mar. 1, 2010;70(5):2075-84. doi: 10.1158/0008-5472. CAN-09-3092. Epub Feb. 16, 2010.

Johannessen et al., A melanocyte lineage program confers resistance to MAP kinase pathway inhibition. Nature. Dec. 5, 2013;504(7478):138-42. doi: 10.1038/nature12688. Epub Jul. 15, 2014. 36 pages.

Johannessen et al., Abstract PR10: A cyclic AMP-regulated melanocyte lineage program confers resistance to MAP kinase pathway inhibition. Mol Cancer Ther. May 12, 2013;PR10. doi: 10.1158/1535-7163.PMS-PR10. 2 pages.

Johannessen et al., Abstract PR5: Identifying mechanisms of drug resistance to MAPK pathway inhibition via genome-scale rescue screens. Clin Cancer Res. May 15, 2012;PR5. doi: 10.1158/1078-0432.MECHRES-PR5. 2 pages.

Johannessen et al., COT drives resistance to RAF inhibition through MAP kinase pathway reactivation. Nature. Dec. 16, 2010;468(7326):968-72. doi: 10.1038/nature09627. Epub Dec. 16, 2010. 16 pages.

Johannessen, Creation and use of the CCSB-Broad Institute Expression Library. Presentation. Jun. 11, 2012. 25 pages.

Joseph et al., The RAF inhibitor PLX4032 inhibits ERK signaling and tumor cell proliferation in a V600E BRAF-selective manner. Proc Natl Acad Sci U S A. Aug. 17, 2010;107(33):14903-8. doi: 10.1073/pnas.1008990107. Epub Jul. 28, 2010.

Kalkers et al., MS functional composite: relation to disease phenotype and disability strata. Neurology. Mar. 28, 2000;54(6):1233-9.—Abstract Only.

Kaplan et al., SHOC2 and CRAF mediate ERK1/2 reactivation in mutant NRAS-mediated resistance to RAF inhibitor. J Biol Chem. Dec. 7, 2012;287(50):41797-807. doi: 10.1074/jbc.M112.390906. Epub Oct. 17, 2012.

Kido et al., Simultaneous suppression of MITF and BRAF V600E enhanced inhibition of melanoma cell proliferation. Cancer Sci. Oct. 2009;100(10):1863-9. doi: 10.1111/j.1349-7006.2009.01266.x. Epub Jun. 29, 2009.

Kono et al., Role of the mitogen-activated protein kinase signaling pathway in the regulation of human melanocytic antigen expression. Mol Cancer Res. Oct. 2006;4(10):779-92.

Kyriakis et al., Raf-1 activates MAP kinase-kinase. Nature. Jul. 30, 1992;358(6385):417-21.—Abstract Only.

Little et al., Amplification of the driving oncogene, KRAS or BRAF, underpins acquired resistance to MEK1/2 inhibitors in colorectal cancer cells. Sci Signal. Mar. 29, 2011;4(166):ra17. doi: 10.1126/scisignal.2001752.—Abstract Only.

Lonze et al., Function and regulation of CREB family transcription factors in the nervous system. Neuron. Aug. 15, 2002;35(4):605-23.

Lopez-Bergami et al., Rewired ERK-JNK signaling pathways in melanoma. Cancer Cell. May 2007;11(5):447-60.

Maruoka et al., Dibutyryl-cAMP up-regulates nur77 expression via histone modification during neurite outgrowth in PC12 cells. J Biochem. Jul. 2010;148(1):93-101. doi: 10.1093/jb/mvq036. Epub Apr. 7, 2010.—Abstract Only.

May, How many species are there on Earth? Science. Sep. 16, 1988;241(4872):1441-9.

McDermott et al., Identification of genotype-correlated sensitivity to selective kinase inhibitors by using high-throughput tumor cell line profiling. Proc Natl Acad Sci U S A. Dec. 11, 2007;104(50):19936-41. Epub Dec. 6, 2007.

Mudduluru et al., PMA up-regulates the transcription of Axl by AP-1 transcription factor binding to TRE sequences via the MAPK cascade in leukaemia cells. Biol. Cell. 2011;103:21-33.

Nazarian et al., Melanomas acquire resistance to B-RAF(V600E) inhibition by RTK or N-RAS upregulation. Nature. Dec. 16, 2010;468(7326):973-7. doi: 10.1038/nature09626. Epub Nov. 24, 2010.

O'Bryan et al., axl, a transforming gene isolated from primary human myeloid leukemia cells, encodes a novel receptor tyrosine kinase. Mol Cell Biol. Oct. 1991;11(10):5016-31.

Patriotis et al., Tpl-2 acts in concert with Ras and Raf-1 to activate mitogen-activated protein kinase. Proc Natl Acad Sci U S A. Oct. 11, 1994;91(21):9755-9.

Pham et al., Characterization of MEK1 phosphorylation by the v-Mos protein. Oncogene. Apr. 20, 1995;10(8):1683-8.—Abstract Only.

Poulikakos et al., RAF inhibitor resistance is mediated by dimerization of aberrantly spliced BRAF(V600E). Nature. Nov. 23, 2011;480(7377):387-90. doi: 10.1038/nature10662.

Price et al., alpha-Melanocyte-stimulating hormone signaling regulates expression of microphthalmia, a gene deficient in Waardenburg syndrome. J Biol Chem. Dec. 4, 1998;273(49):33042-7.

Rylova et al., The CLN3 gene is a novel molecular target for cancer drug discovery. Cancer Res. Feb. 1, 2002;62(3):801-8.

(56) References Cited

OTHER PUBLICATIONS

Saito-Hisaminato et al., Genome-wide profiling of gene expression in 29 normal human tissues with a cDNA microarray. DNA Res. Apr. 30, 2002;9(2):35-45.
Schwartz et al., A phase I study of XL281, a selective oral RAF kinase inhibitor, in patients (Pts) with advanced solid tumors. Journal of Clinical Oncology, 2009 ASCO Annual Meeting Proceedings. May 2009;27(15S) Abstract No. 3513.
Sensi et al., Human cutaneous melanomas lacking MITF and melanocyte differentiation antigens express a functional Axl receptor kinase. J Invest Dermatol. Dec. 2011;131(12):2448-57. doi: 10.1038/jid.2011.218.
Shi et al., Melanoma whole-exome sequencing identifies (V600E)B-RAF amplification-mediated acquired B-RAF inhibitor resistance. Nat Commun. Mar. 6, 2012;3:724. doi: 10.1038/ncomms1727.
Smith et al., Regulation of NR4A nuclear receptor expression by oncogenic BRAF in melanoma cells. Pigment Cell Melanoma Res. Jun. 2011;24(3):551-63. doi: 10.1111/j.1755-148X.2011.00843.x. Epub Mar. 31, 2011.—Abstract Only.
Solit et al., BRAF mutation predicts sensitivity to MEK inhibition. Nature. Jan. 19, 2006;439(7074):358-62. Epub Nov. 6, 2005.
Straussman et al., Tumour micro-environment elicits innate resistance to RAF inhibitors through HGF secretion. Nature. Jul. 26, 2012;487(7408):500-4. doi: 10.1038/nature11183.
Tissing et al., Genomewide identification of prednisolone-responsive genes in acute lymphoblastic leukemia cells. Blood. May 1, 2007;109(9):3929-35. Epub Jan. 11, 2007.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsao et al., Melanoma: from mutations to medicine. Genes Dev. Jun. 1, 2012;26(11):1131-55. doi: 10.1101/gad.191999.112.
Vigil et al., Ras superfamily GEFs and GAPs: validated and tractable targets for cancer therapy? Nat Rev Cancer. Dec. 2010;10(12):842-57. doi: 10.1038/nrc2960. Epub Nov. 24, 2010.
Villanueva et al., Acquired resistance to BRAF inhibitors mediated by a RAF kinase switch in melanoma can be overcome by cotargeting MEK and IGF-1R/PI3K. Cancer Cell. Dec. 14, 2010;18(6):683-95. doi: 10.1016/j.ccr.2010.11.023.
Wagle et al., Dissecting therapeutic resistance to RAF inhibition in melanoma by tumor genomic profiling. J Clin Oncol. Aug. 1, 2011;29(22):3085-96. doi: 10.1200/JCO.2010.33.2312. Epub Mar. 7, 2011.
Walton et al., A dominant repressor of cyclic adenosine 3',5'-monophosphate (cAMP)-regulated enhancer-binding protein activity inhibits the cAMP-mediated induction of the somatostatin promoter in vivo. Mol Endocrinol. Apr. 1992;6(4):647-55.—Abstract Only.
Wan et al., Mechanism of activation of the RAF-ERK signaling pathway by oncogenic mutations of B-RAF. Cell. Mar. 19, 2004;116(6):855-67.
Wang et al., Detection and characterization of EWSR1/ATF1 and EWSR1/CREB1 chimeric transcripts in clear cell sarcoma (melanoma of soft parts). Mod Pathol. Sep. 2009;22(9):1201-9. doi: 10.1038/modpathol.2009.85. Epub Jun. 26, 2009.
Wang et al., G protein-coupled receptor 30 in tumor development. Endocrine. Aug. 2010;38(1):29-37. doi: 10.1007/s12020-010-9363-z. Epub Jul. 8, 2010. Review.
Wellbrock et al., Oncogenic BRAF regulates melanoma proliferation through the lineage specific factor MITF. PLoS One. Jul. 16, 2008;3(7):e2734. doi: 10.1371/journal.pone.0002734.
Wellbrook et al., V599EB-RAF is an oncogene in melanocytes. Cancer Res. Apr. 1, 2004;64(7):2338-42.
Wood et al., MicroScale screening reveals genetic modifiers of therapeutic response in melanoma. Sci Signal. May 15, 2012;5(224):rs4. doi: 10.1126/scisignal.2002612.
Wu et al., c-Kit triggers dual phosphorylations, which couple activation and degradation of the essential melanocyte factor Mi. Genes Dev. Feb. 1, 2000;14(3):301-12.
Xiao, Beta-adrenergic signaling in the heart: dual coupling of the beta2-adrenergic receptor to G(s) and G(i) proteins. Sci STKE. Oct. 16, 2001;2001(104):re15.—Abstract Only.
Yang et al., A public genome-scale lentiviral expression library of human ORFs. Nat Methods. Jun. 26, 2011;8(8):659-61. doi: 10.1038/nmeth.1638.
Yokoyama et al., Pharmacologic suppression of MITF expression via HDAC inhibitors in the melanocyte lineage. Pigment Cell Melanoma Res. Aug. 2008;21(4):457-63. doi: 10.1111/j.1755-148X.2008.00480.x. Epub Jun. 27, 2008.
Zipser et al., A proliferative melanoma cell phenotype is responsive to RAF/MEK inhibition independent of BRAF mutation status. Pigment Cell Melanoma Res. Apr. 2011;24(2):326-33. doi: 10.1111/j.1755-148X.2010.00823.x. Epub Jan. 12, 2011.

* cited by examiner

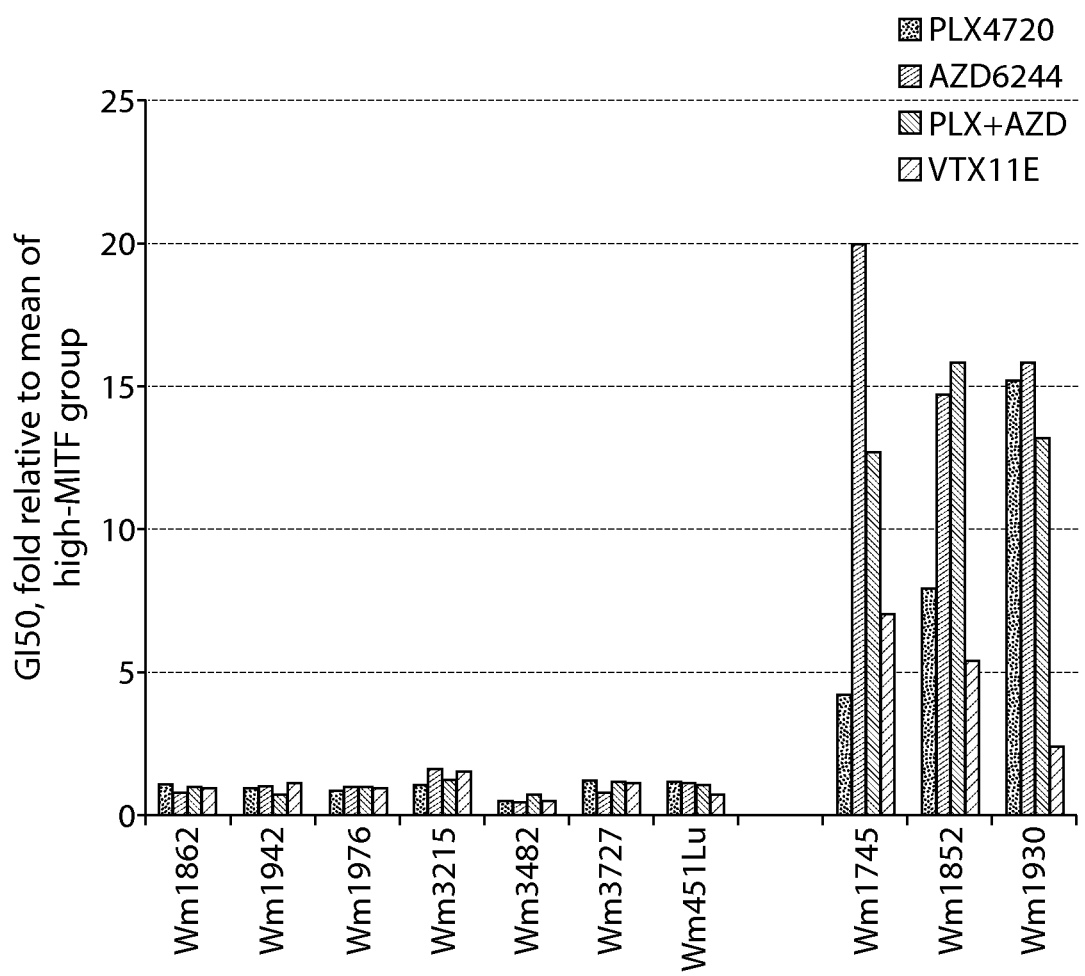

METHODS OF IDENTIFYING RESPONSES TO MAP KINASE INHIBITION THERAPY

CROSS-REFERENCE TO RELATED APPLICATIONS

This application claims the benefit of the filing date of U.S. Provisional Application No. 61/800,304, filed Mar. 15, 2013, the entire contents of which are incorporated by reference herein.

BACKGROUND OF INVENTION

Oncogenic mutations in the serine/threonine kinase B-RAF (also known as BRAF) are found in 50-70% of malignant melanomas. (Davies, H. et al., Nature 417, 949-954 (2002).) Pre-clinical studies have demonstrated that the B-RAF (V600E) mutation predicts a dependency on the mitogen-activated protein kinase (MAPK) signaling cascade in melanoma (Hoeflich, K. P. et al., Cancer Res. 69, 3042-3051 (2009); McDermott, U. et al., Proc. Natl Acad. Sci. USA 104, 19936-19941 (2007); Solit, D. B. et al. BRAF mutation predicts sensitivity to MEK inhibition. Nature 439, 358-362 (2006); Wan, P. T. et al., Cell 116, 855-867 (2004); Wellbrock, C. et al., Cancer Res. 64, 2338-2342 (2004))—an observation that has been validated by the success of RAF or MEK inhibitors in clinical trials (Flaherty, K. T. et al., N. Engl. J. Med. 363, 809-819 (2010); Infante, J. R. et al., J. Clin. Oncol. 28 (suppl.), 2503 (2010); Schwartz, G. K. et al., J. Clin. Oncol. 27 (suppl.), 3513 (2009).)

However, clinical responses to targeted anticancer therapeutics are frequently confounded by intrinsic or acquired resistance. (Engelman, J. A. et al., Science 316, 1039-1043 (2007); Gorre, M. E. et al., Science 293, 876-880 (2001); Heinrich, M. C. et al., J. Clin. Oncol. 24, 4764-4774 (2006); Daub, H., Specht, K. & Ullrich, A. Nature Rev. Drug Discov. 3, 1001-1010 (2004).) Accordingly, there remains a need for new methods for identification of resistance mechanisms in a manner that elucidates "druggable" targets for effective short- and long-term treatment strategies, for new methods of identifying patients that are likely to benefit from the treatment strategies, and for methods of treating patients with the effective short- and long-term treatment strategies.

SUMMARY OF INVENTION

The present invention relates, in part, to the identification of molecular signatures that are associated with and thus are predictive of resistance or sensitivity of particular cancers, such as BRAF mutant melanomas, to particular treatments, such as MAPK pathway inhibitors. The present invention also relates, in part, to the identification of further therapeutic targets for such cancers wherein such targets may be modified in order to establish or maintain a sensitive state in such cancers. The invention further embraces screening assays that can be used to identify agents that promote a sensitive phenotype or agents that promote a resistant phenotype, or agents that maintain a sensitive phenotype in the long term and/or following exposure to a MAPK pathway inhibitor.

The invention is based in part on the identification of markers and more importantly collections of markers, referred to herein as signatures or profiles, that are associated with resistance (and/or increased likelihood of resistance) or sensitivity (and/or increased likelihood of sensitivity to MAPK pathway inhibitor therapy. The invention therefore provides methods that use one or more of the signatures provided herein as diagnostic, theranostic and/or prognostic markers. Such signatures also provide additional treatment targets. These various methods are described herein in greater detail.

The invention provides in another aspect a method for screening a molecular or chemical library, including for example a combinatorial library, to identify an agent or combination of agents that (1) convert a sensitive signature in a cancer cell or population of cancer cells to a resistant signature, (2) convert a resistant signature in a cancer cell or population of cancer cells to a sensitive signature, (3) maintain a sensitive signature in a cancer cell or population of cancer cells for example for an extended period of time and/or indefinitely, and/or (4) maintain a sensitive signature in a cancer cell or population of cancer cells in the presence of a MAPK pathway inhibitor.

Diagnostic, prognostic, and theranostic assays of the invention involve assaying mRNA expression and/or protein expression of one and typically more than one marker of those provided herein in order to arrive at a signature of resistance or sensitivity. In some embodiments, these methods may include assaying gene copy number for one or more markers and/or assaying activity level of one or more markers. The art is familiar with assays for copy number, mRNA expression levels, protein expression levels, and activity levels of the one or more markers as described herein. Non-limiting examples of such assays are described herein.

Thus, in one aspect, the invention provides a method comprising measuring in a cancer sample obtained from a subject having cancer (1) expression of one or more resistance markers selected from the group consisting of BDNF, KCNMA1, PAPPA, CCDC80, RRAS, CLMP, EPHA2, HRH1, SCG5, TSPAN5, BEX1, TMEM200A, TGM2, CD163L1, S100A16, IGFBP6, ITGA3, LOC100130938, C12orf75, FBN2, CRIM1, COL6A2, and EFNB2 ("R1 markers"), and (2) expression of
(a) one or more resistance markers selected from the group consisting of DSE, CYR61, CDH13, PODXL, SERPINE1, NRP1, IL1B, BIRC3, AXL, NUAK1, TCF4, COL5A1, NTM, CCL2, IL1A and TPM1 ("R2 markers"), or
(b) one or more sensitive markers selected from the group consisting of IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A ("S1 markers"), or
(c) one or more sensitive markers selected from the group consisting of GYG2, TYR, SLC45A2, PLA1A, ST3GAL6, DCT, CITED1, RAB38, TNFRSF14, GALNT3, MREG, GPM6B, RRAGD, CAPN3, MLANA, and MITF ("S2 markers"), and identifying the cancer as resistant to a MAPK pathway inhibitor if
(i) one or more of the R1 markers is up-regulated and
(ii) one or more of the R2 markers is up-regulated or
(iii) one or more of the S1 markers is down-regulated or
(iv) one or more of the S2 markers is down-regulated, or identifying the cancer as sensitive to a MAPK pathway inhibitor if
(i) one or more of the R1 markers is down-regulated and
(ii) one or more of the R2 markers is down-regulated or
(iii) one or more of the S1 markers is up-regulated or
(iv) one or more of the S2 markers is up-regulated.

In another aspect, the invention provides a method comprising measuring in a cancer sample obtained from a subject having cancer (1) expression of one or more sensitive markers selected from the group consisting of IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A ("S1 markers"), and (2) expression of
  (a) one or more sensitive markers selected from the group consisting of GYG2, TYR, SLC45A2, PLA1A, ST3GAL6, DCT, CITED1, RAB38, TNFRSF14, GALNT3, MREG, GPM6B, RRAGD, CAPN3, MLANA, and MITF ("S2 markers"), or
  (b) expression of one or more resistance markers selected from the group consisting of BDNF, KCNMA1, PAPPA, CCDC80, RRAS, CLMP, EPHA2, HRH1, SCG5, TSPAN5, BEX1, TMEM200A, TGM2, CD163L1, S100A16, IGFBP6, ITGA3, LOC100130938, C12orf75, FBN2, CRIM1, COL6A2, and EFNB2 ("R1 markers"), or
  (c) one or more resistance markers selected from the group consisting of DSE, CYR61, CDH13, PODXL, SERPINE1, NRP1, IL1B, BIRC3, AXL, NUAK1, TCF4, COL5A1, NTM, CCL2, IL1A and TPM1 ("R2 markers"), and identifying the cancer as sensitive to a MAPK pathway inhibitor if
  (i) one or more of the S1 markers is up-regulated and
  (ii) one or more of the S2 markers is up-regulated or
  (iii) one or more of the R1 markers is down-regulated or
  (iv) one or more of the R2 markers is down-regulated.

In another aspect, the invention provides a method comprising measuring in a cancer sample obtained from a subject having cancer (1) expression of two or more resistance markers selected from the group consisting of BDNF, KCNMA1, PAPPA, CCDC80, RRAS, CLMP, EPHA2, HRH1, SCG5, TSPAN5, BEX1, TMEM200A, TGM2, CD163L1, S100A16, IGFBP6, ITGA3, LOC100130938, C12orf75, FBN2, CRIM1, COL6A2, and EFNB2 ("R1 markers"), and/or (2) expression of two or more sensitive markers selected from the group consisting of IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A ("S1 markers"), and identifying the cancer as resistant to a MAPK pathway inhibitor if
  (i) two or more of the R1 markers is up-regulated, and optionally
  (ii) two or more of the S1 markers is down-regulated, or identifying the cancer as sensitive to a MAPK pathway inhibitor if
  (i) two or more of the S1 markers is up-regulated, and optionally
  (ii) two or more of the R1 markers is down-regulated.

In some embodiments, the subject is human.
In some embodiments, the cancer is a cancer treated with a MAPK pathway inhibitor. In some embodiments, the cancer is melanoma. In some embodiments, the cancer comprises a BRAF mutation. In some embodiments, the cancer is a melanoma having a BRAF mutation. In some embodiments, the subject has been or is being treated with a MAPK pathway inhibitor.

In some embodiments, expression is mRNA expression. In some embodiments, expression is protein expression.

In some embodiments, the method further comprises altering a therapy to the subject if the subject presents a resistant phenotype.

In another aspect, the invention provides a method comprising measuring in a cancer sample obtained from a subject having cancer (1) one or more sensitive markers selected from the group consisting of IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A ("S1 markers"), and (2) expression of
  (a) one or more sensitive markers selected from the group consisting of GYG2, TYR, SLC45A2, PLA1A, ST3GAL6, DCT, CITED1, RAB38, TNFRSF14, GALNT3, MREG, GPM6B, RRAGD, CAPN3, MLANA, and MITF ("S2 markers"), or
  (b) expression of one or more resistance markers selected from the group consisting of BDNF, KCNMA1, PAPPA, CCDC80, RRAS, CLMP, EPHA2, HRH1, SCG5, TSPAN5, BEX1, TMEM200A, TGM2, CD163L1, S100A16, IGFBP6, ITGA3, LOC100130938, C12orf75, FBN2, CRIM1, COL6A2, and EFNB2 ("R1 markers"), or
  (c) one or more resistance markers selected from the group consisting of DSE, CYR61, CDH13, PODXL, SERPINE1, NRP1, IL1B, BIRC3, AXL, NUAK1, TCF4, COL5A1, NTM, CCL2, IL1A and TPM1 ("R2 markers"), and administering an effective amount of a MAPK pathway inhibitor to the subject if
  (i) one or more of the S1 markers is up-regulated and
  (ii) one or more of the S2 markers is up-regulated or
  (iii) one or more of the R1 markers is down-regulated or
  (iv) one or more of the R2 markers is down-regulated.

In another aspect, the invention provides a method comprising measuring in a cancer sample obtained from a subject having cancer (1) expression of two or more resistance markers selected from the group consisting of BDNF, KCNMA1, PAPPA, CCDC80, RRAS, CLMP, EPHA2, HRH1, SCG5, TSPAN5, BEX1, TMEM200A, TGM2, CD163L1, S100A16, IGFBP6, ITGA3, LOC100130938, C12orf75, FBN2, CRIM1, COL6A2, and EFNB2 ("R1 markers"), and/or (2) expression of two or more sensitive markers selected from the group consisting of IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A ("S1 markers"), and administering an effective amount of a MAPK pathway inhibitor to the subject if
  (i) two or more of the S1 markers is up-regulated, and optionally
  (ii) two or more of the R1 markers is down-regulated.

In some embodiments, the subject is human.
In some embodiments, the cancer is melanoma.
In some embodiments, the cancer comprises a BRAF mutation. In some embodiments, the BRAF mutation comprises a V600E mutation.

In some embodiments, expression is mRNA expression. In some embodiments, expression is protein expression.

In some embodiments, the MAPK pathway inhibitor is a RAF inhibitor. In some embodiments, the MAPK pathway inhibitor is a MEK inhibitor. In some embodiments, the MAPK pathway inhibitor is an ERK inhibitor. In some embodiments, the MAPK pathway inhibitor is a first and a second MAPK pathway inhibitor, wherein the first MAPK pathway inhibitor is a RAF inhibitor and the second MAPK pathway inhibitor is a MEK inhibitor.

In another aspect, the invention provides a method comprising measuring, in a cancer cell or population of cancer cells, a first expression level of one or more R1 markers, and one or more R2 markers, S1 markers, or one or more S2 markers;

measuring, in a cancer cell or population of cancer cells in the presence of at least one agent, a second expression level of one or more R1 markers and one or more R2 markers, S1 markers, or one or more S2 markers; and identifying the agent as capable of converting a sensitive signature in the cancer cell or population of cancer cells to a resistant signature if
  (i) the second expression level of the one or more of the R1 markers is up-regulated compared to the first expression level and
  (ii) the second expression level of the one or more of the R2 markers is up-regulated compared to the first expression level or
  (iii) the second expression level of the one or more of the S1 markers is down-regulated compared to the first expression level or
  (iv) the second expression level of the one or more of the S2 markers is down-regulated compared to the first expression level, or identifying the agent as capable of converting a resistant signature in the cancer cell or population of cancer cells to a sensitive signature if
  (i) the second expression level of the one or more of the R1 markers is down-regulated compared to the first expression level and
  (ii) the second expression level of the one or more of the R2 markers is down-regulated compared to the first expression level or
  (iii) the second expression level of the one or more of the S1 markers is up-regulated compared to the first expression level or
  (iv) the second expression level of the one or more of the S2 markers is up-regulated compared to the first expression level.

In another aspect, the invention provides a method comprising measuring, in a cancer cell or population of cancer cells, a first expression level of two or more R1 markers and/or two or more S1 markers; measuring, in a cancer cell or population of cancer cells in the presence of at least one agent, a second expression level of one or more R1 markers and one or more R2 markers, S1 markers, or one or more S2 markers; and identifying the agent as capable of converting a sensitive signature in the cancer cell or population of cancer cells to a resistant signature if
  (i) the second expression level of the two or more of the R1 markers is up-regulated compared to the first expression level, and optionally
  (ii) the second expression level of the two or more of the S1 markers is down-regulated compared to the first expression level, or identifying the agent as capable of converting a resistant signature in the cancer cell or population of cancer cells to a sensitive signature if
  (i) the second expression level of the two or more of the S1 markers is up-regulated compared to the first expression level, and optionally
  (ii) the second expression level of the two or more of the R1 markers is down-regulated compared to the first expression level.

In another aspect, the invention provides a method comprising measuring, in a cancer cell or population of cancer cells, a first expression level of one or more S1 markers, and one or more S2 markers, R1 markers, or one or more R2 markers;

measuring, in a cancer cell or population of cancer cells in the presence of at least one agent, a second expression level of one or more S1 markers and one or more S2 markers, R1 markers, or one or more R2 markers; and identifying the agent as capable of converting a resistant signature in the cancer cell or population of cancer cells to a sensitive signature if
  (i) the second expression level of the one or more of the S1 markers is up-regulated compared to the first expression level and
  (ii) the second expression level of the one or more of the S2 markers is up-regulated compared to the first expression level or
  (iii) the second expression level of the one or more of the R1 markers is down-regulated compared to the first expression level or
  (iv) the second expression level of the one or more of the R2 markers is down-regulated compared to the first expression level.

In another aspect, the invention provides a method comprising measuring, in a cancer cell or population of cancer cells, a first expression level of one or more S1 markers, and one or more S2 markers, R1 markers, or one or more R2 markers;

measuring, in a cancer cell or population of cancer cells in the presence of a MAPK pathway inhibitor and at least one agent, a second expression level of one or more S1 markers and one or more S2 markers, R1 markers, or one or more R2 markers; and identifying the agent as capable of maintaining a sensitive signature in a cancer cell or population of cancer cells in the presence of a MAPK pathway inhibitor if
  (i) the second expression level of the one or more of the S1 markers is up-regulated compared to the first expression level and
  (ii) the second expression level of the one or more of the S2 markers is up-regulated compared to the first expression level or
  (iii) the second expression level of the one or more of the R1 markers is down-regulated compared to the first expression level or
  (iv) the second expression level of the one or more of the R2 markers is down-regulated compared to the first expression level.

In some embodiments, the MAPK pathway inhibitor is a RAF inhibitor. In some embodiments, the MAPK pathway inhibitor is a MEK inhibitor. In some embodiments, the MAPK pathway inhibitor is an ERK inhibitor.

In some embodiments, the agent is a member of a molecular library.

In some embodiments, the cancer cell or population of cancer cells comprises a B-RAF mutation. In some embodiments, the B-RAF mutation is V600E. In some embodiments, the cancer cell or population of cancer cells is a melanoma cell or population of melanoma cells.

These and other aspects and embodiments of the invention will now be described in greater detail.

BRIEF DESCRIPTION OF DRAWINGS

FIG. 1 is a graph of the GI50 for a RAF inhibitor (PLX4720), a MEK inhibitor (AZD6244), a combination of the RAF and MEK inhibitor, and an ERK inhibitor (VTX11e) in each patient derived short term culture used in the validation study. For each group on the x-axis, the bars are, from left to right, PLX4720, AZD6244, PLX+AZD, and VTX11E.

DETAILED DESCRIPTION OF INVENTION

The invention provides molecular profiles (or signatures) for particular cancers that are or are likely to be resistant to therapy with a MAPK pathway inhibitor. The invention further provides molecular profiles (or signatures) for cancers that are or are likely to be sensitive (or susceptible) to therapy with a MAPK pathway inhibitor. MAPK pathway inhibitor therapy is typically used in the treatment of melanoma, and more particularly in the treatment of BRAF mutant melanoma. Thus, the invention provides a molecular profile of melanoma subtypes that are or are likely to be resistant or sensitive to MAPK pathway inhibitor therapy.

The invention is premised in part on the identification of molecular subtypes of melanoma that are either intrinsically resistant or intrinsically sensitive to MAPK pathway inhibitor treatment. As described herein, a signature of genes was identified whose expression was well-correlated with sensitivity or resistance in melanoma cells that were intrinsically resistant or sensitive to a MAPK pathway inhibitor. Genes whose expression was well-correlated with sensitivity or resistance were identified based on an expression pattern across cell lines that was strongly correlated (r>0.6, identifying markers of resistance) or anti-correlated (r<−0.6, identifying markers of sensitivity) with the IC50 values for the RAF inhibitor PLX4720 in the same cell lines. These various groupings of markers are listed in Table 1.

TABLE 1

Resistance and Sensitivity Markers

| Resistant | validation dataset: rank as marker of resistance | Sensitive | validation dataset: rank as marker of sensitivity |
| --- | --- | --- | --- |
| BDNF | 82 | IGSF11 | #N/A |
| KCNMA1 | 374 | FAM167B | #N/A |
| DSE | #N/A | MTUS1 | 170 |
| PAPPA | 102 | GYG2 | 26 |
| CYR61 | 18 | GDF15 | 280 |
| CCDC80 | #N/A | LINC00518 | #N/A |
| CDH13 | 845 | TYR | 42 |
| RRAS | 167 | LRRK2 | #N/A |
| PODXL | 123 | ID4 | 58 |
| CLMP | #N/A | CMTM8 | 7046 |
| SERPINE1 | 61 | KIAA0226L | #N/A |
| EPHA2 | 236 | C11orf96 | #N/A |
| NRP1 | 35 | D4S234E | 19 |
| HRH1 | 426 | SLC45A2 | 10 |
| SCG5 | 27 | TBC1D16 | 49 |
| TSPAN5 | 217 | TTYH2 | #N/A |

TABLE 1-continued

Resistance and Sensitivity Markers

| Resistant | validation dataset: rank as marker of resistance | Sensitive | validation dataset: rank as marker of sensitivity |
| --- | --- | --- | --- |
| IL1B | 13 | LAMA1 | 1951 |
| BEX1 | 60 | PMEL | #N/A |
| TMEM200A | #N/A | PROS1 | 310 |
| BIRC3 | 430 | PLA1A | 63 |
| AXL | 12 | KCNN2 | 54 |
| TGM2 | 97 | ESRP1 | #N/A |
| CD163L1 | #N/A | ST3GAL6 | 79 |
| S100A16 | #N/A | DCT | 6 |
| NUAK1 | 139 | TRIM63 | #N/A |
| TCF4 | 483 | CITED1 | 57 |
| IGFBP6 | 103 | RAB38 | 66 |
| COL5A1 | 407 | RXRG | 137 |
| ITGA3 | 171 | TNFRSF14 | 60 |
| NTM | #N/A | PLEKHH1 | #N/A |
| LOC100130938 | #N/A | CPN1 | 45 |
| C12orf75 | #N/A | PI15 | 73 |
| FBN2 | 28 | GNPTAB | 234 |
| CRIM1 | 33 | GALNT3 | 13 |
| TPM1 | 119 | MREG | #N/A |
| COL6A2 | 289 | GPM6B | 25 |
| CCL2 | 11 | RRAGD | 214 |
| EFNB2 | 88 | CAPN3 | 18 |
| IL1A | 290 | MLANA | 2 |
|  |  | RNF144A | #N/A |
|  |  | MITF | 14 |

NA = not measured

Thus, differential expression profiling was used to identify a molecular subtype of melanoma that is intrinsically resistant to MAPK pathway inhibition. In BRAF-mutant melanoma, pharmacologic sensitivity data and steady-state gene expression profiling data identified expression of, inter alia, BDNF, SCGC5, AXL and gene signatures associated with NF-kB pathway activation and no expression of, inter alia, SLC45A2, GYG2, MITF and its corresponding target genes including for example SILVER (SLV), tyrosinase related protein 1 (TRP1), Melan-A (MelA), and dopachrome tautomerase (DCT). This combination of positive resistance marker expression in the absence of sensitivity marker expression was identified as a molecular signature predictive of resistance to MAPK pathway inhibitors.

Also as described herein, these putative markers of sensitivity and resistance were validated in an independent collection of BRAF_V600-mutant patient-derived melanoma short-term cultures. It was predicted that MAPK-inhibitor resistant short-term cultures would show low expression of markers associated with sensitivity and high expression of markers associated with resistance. Table 1 lists the relative rank of the sensitivity and resistance markers in the validation dataset. Accordingly, in some embodiments markers are selected from those above a certain rank as listed in Table 1. For example, markers may be selected that are above a rank of 5,000, 1,000, 500, 200, 100, 50, 40, 30, 20, or 15 as indicated in Table 1.

Thus in some embodiments, a resistant cancer is identified based in whole or in part on this signature. The invention contemplates signatures that comprise these markers in whole or in part, including signatures which comprise additional markers that are up-regulated or down-regulated in resistant melanoma.

The invention further contemplates that the resistant phenotype is a reversible state that can be modified and thus reverted to a sensitive state. It is contemplated that neither the sensitive nor the resistant phenotypes are fixed states, in some instances. It is contemplated herein that establishment and/or maintenance of the sensitive signature and of sensitivity may be effected by or may require expression or amplification of MITF, cAMP signaling, and/or other markers of sensitivity alone or in combination, and that establishment and/or maintenance of the resistant signature and/or of resistance may be effected by or may require expression or amplification of AXL, NF-kB signaling, aberrant MAPK signaling, and/or other markers of resistance alone or in combination. Accordingly, the invention further embraces methods for monitoring and modifying the "state" of a cancer such as melanoma before and after treatment with a MAPK pathway inhibitor. Such modification may involve inducing the expression of one or more sensitive markers in the cancer cells or down-regulating the expression of one or more resistant markers in the cancer cells. In this regard, the resistant markers are considered to be targets of therapy in addition to markers of a particular phenotype.

Certain aspects of the invention are directed towards identifying a molecular signature of a cancer and based on that signature predicting whether the cancer is more likely to be resistant or more likely to be sensitive to therapy with a MAPK pathway inhibitor.

The molecular signatures are typically expression signatures or profiles. They may be mRNA profiles or they may be protein profiles or they may be a combination thereof. The profiles may comprise 2 or more markers. The profiles may comprise 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 414, 42, 43, 44, 45, 46, 47, 48, 49, 50 or more markers. The markers may be all resistant markers (as described below), all sensitive markers (as described below), or any combination thereof. The markers may be analyzed individually or together on for example an array as described in greater detail herein. Typically, most expression analyses are carried out using cancer cell populations, although in some instance they may be carried out using a single cancer cell. The invention intends to embrace both situations.

As used herein, a cancer that is or is more likely to be resistant to therapy with a MAPK pathway inhibitor has a resistant phenotype. Resistance to MAPK pathway inhibition, as used herein, refers to resistance to inhibition of the MAPK pathway and thus includes resistance to inhibition to any or all of RAF, MEK, RAF+MEK, and ERK. Conversely, a cancer that is or is more likely to be sensitive to therapy with a MAPK pathway inhibitor has a sensitive phenotype.

Resistance Markers

Up-regulated expression of certain markers is associated with the resistant phenotype. These markers are referred to herein as resistance markers. These markers are BDNF, KCNMA1, PAPPA, CCDC80, RRAS, CLMP, EPHA2, HRH1, SCG5, TSPAN5, BEX1, TMEM200A, TGM2, CD163L1, S100A16, IGFBP6, ITGA3, LOC100130938, C12orf75, FBN2, CRIM1, COL6A2, and EFNB2. These markers are referred to as R1 markers in the context of this disclosure. The invention contemplates that increased expression of any one of these markers alone can be used to predict whether a cancer has a resistant phenotype.

Up-regulated expression of other markers is also associated with the resistant phenotype. These markers are also referred to herein as resistance markers. These markers are DSE, CYR61, CDH13, PODXL, SERPINE1, NRP1, IL1B, BIRC3, AXL, NUAK1, TCF4, COL5A1, NTM, CCL2, IL1A and TPM1. These markers are referred to as R2 markers in the context of this disclosure. The invention contemplates that increased expression of any one of these markers together with one or more other markers disclosed herein can be used to predict whether a cancer has a resistant phenotype. In some embodiments, the R2 marker is used together with an up-regulated R1 marker or a down-regulated S1 marker, or a down-regulated S2 marker. In some embodiments, the R2 marker is used together with an up-regulated R1 marker or a down-regulated S1 marker.

All of the foregoing resistance markers are at least 4-fold up-regulated in resistant cells relative to sensitive cells, such as a median difference >2 (log 2 units) between a group of resistant cell lines (HS294T, LOXIMVI, RPMI7951, WM793, IGR39, A2058) and a group of sensitive cell lines (WM88, UACC62, SKMEL5, WM983B, COLO679, RVH421, G361, WM2664).

A resistant signature may comprise up-regulated expression of one or more R1 markers, optionally with
  (1) up-regulation of one or more R2 markers (e.g., AXL), and/or
  (2) down-regulation of one or more S1 markers, and/or
  (3) down-regulation of one or more S2 markers (e.g., MITF and/or its targets such as but not limited to SILVER (SLV)).

A resistant signature may comprise up-regulated expression of one or more R2 markers (e.g., AXL), optionally with
  (1) down-regulation of one or more S1 markers, and/or
  (2) down-regulation of one or more S2 markers (e.g., MITF and/or its targets such as but not limited to SILVER (SLV)).

A resistant signature may comprise up-regulated expression of one or more R2 markers (e.g., AXL), optionally with down-regulation of one or more S2 markers (e.g., MITF and/or its targets such as but not limited to SILVER (SLV)).

Sensitivity Markers

Up-regulated expression of certain markers is associated with the sensitive phenotype. These markers are referred to herein as sensitivity markers. These markers are IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A. These markers are referred to as S1 markers in the context of this disclosure. The invention contemplates that increased expression of any one of these markers alone can be used to predict whether a cancer has a sensitive phenotype.

Up-regulated expression of other markers is also associated with the sensitive phenotype. These markers are also referred to herein as sensitivity markers. These markers are GYG2, TYR, SLC45A2, PLA1A, ST3GAL6, DCT, CITED1, RAB38, TNFRSF14, GALNT3, MREG, GPM6B, RRAGD, CAPN3, MLANA, and MITF. These markers are referred to as S2 markers in the context of this disclosure. The invention contemplates that increased expression of any one of these markers together with one or more other markers disclosed herein can be used to predict whether a cancer has a sensitive phenotype. In some embodiments, the S2 marker is used together with an up-regulated S1 marker or a down-regulated R1 marker, or a down-regulated R2 marker. In some embodiments, the S2 marker is used together with an up-regulated S1 marker or a down-regulated R1 marker.

All of the foregoing resistance markers are at least 4-fold up-regulated in sensitive cells relative to resistant cells, such as a median difference >2 (log 2 units) between a group of sensitive cell lines (WM88, UACC62, SKMEL5, WM983B, COLO679, RVH421, G361, WM2664) and a group of resistant cell lines (HS294T, LOXIMVI, RPMI7951, WM793, IGR39, A2058).

A sensitive signature may comprise up-regulated expression of one or more S1 markers, optionally with
(1) up-regulation of one or more S2 markers (e.g., MITF and/or its targets such as but not limited to SILVER (SLV)), and/or
(2) down-regulation of one or more R1 markers, and/or
(3) down-regulation of one or more R2 markers (e.g., AXL).

A sensitive signature may comprise up-regulated expression of one or more S2 markers (e.g., MITF and/or its targets such as but not limited to SILVER (SLV)), optionally with
(1) down-regulation of one or more R1 markers, and/or
(2) down-regulation of one or more R2 markers (e.g., AXL).

A sensitive signature may comprise up-regulated expression of one or more S2 markers (e.g., MITF and/or its targets such as but not limited to SILVER (SLV)), optionally with down-regulation of one or more R2 markers (e.g., AXL).

Gene identifiers for the resistance and sensitivity markers are provided in Table 2.

TABLE 2

| | Human Gene Entrez ID | Transcript IDs |
|---|---|---|
| Resistant | | |
| BDNF | 627 | NM_001143805.1 |
| | | NM_001143806.1 |
| | | NM_001143807.1 |
| | | NM_001143808.1 |
| | | NM_001143809.1 |
| | | NM_001143810.1 |
| | | NM_001143811.1 |
| | | NM_001143812.1 |
| | | NM_001143813.1 |
| | | NM_001143814.1 |
| | | NM_001143816.1 |
| | | NM_001709.4 |
| | | NM_170731.4 |
| | | NM_170732.4 |
| | | NM_170733.3 |
| | | NM_170734.3 |
| | | NM_170735.5 |
| KCNMA1 | 3778 | NM_001014797.2 |
| | | NM_001161352.1 |
| | | NM_001161353.1 |
| | | NM_001271518.1 |
| | | NM_001271519.1 |
| | | NM_001271520.1 |
| | | NM_001271521.1 |
| | | NM_001271522.1 |
| | | NM_002247.3 |
| DSE | 29940 | NM_001080976.1 |
| | | NM_013352.2 |
| PAPPA | 5069 | NM_002581.3 |
| CYR61 | 3491 | NM_001554.4 |
| CCDC80 | 151887 | NM_199511.1 |
| | | NM_199512.1 |
| CDH13 | 1012 | NM_001220488.1 |
| | | NM_001220489.1 |
| | | NM_001220490.1 |
| | | NM_001220491.1 |
| | | NM_001220492.1 |
| | | NM_001257.4 |
| RRAS | 6237 | NM_006270.3 |
| PODXL | 5420 | NM_001018111.2 |
| | | NM_005397.3 |
| CLMP | 79827 | NM_024769.2 |
| SERPINE1 | 5054 | NM_000602.4 |
| | | NM_001165413.2 |
| EPHA2 | 1969 | NM_004431.3 |
| NRP1 | 8829 | NM_001024628.2 |
| | | NM_001024629.2 |
| | | NM_001244972.1 |
| | | NM_001244973.1 |
| | | NM_003873.5 |
| HRH1 | 3269 | NM_000861.3 |
| | | NM_001098211.1 |
| | | NM_001098212.1 |
| | | NM_001098213.1 |
| SCG5 | 6447 | NM_001144757.1 |
| | | NM_003020.3 |
| TSPAN5 | 10098 | NM_005723.3 |
| IL1B | 3553 | NM_000576.2 |
| BEX1 | 55859 | NM_018476.3 |
| TMEM200A | 114801 | NM_001258276.1 |
| | | NM_001258277.1 |
| | | NM_001258278.1 |
| | | NM_052913.2 |
| BIRC3 | 330 | NM_001165.4 |
| | | NM_182962.2 |
| AXL | 558 | NM_001699.4 |
| | | NM_021913.3 |
| TGM2 | 7052 | NM_004613.2 |
| | | NM_198951.1 |
| CD163L1 | 283316 | NM_174941.4 |
| S100A16 | 140576 | NM_080388.1 |
| NUAK1 | 9891 | NM_014840.2 |
| TCF4 | 6925 | NM_001083962.1 |
| | | NM_001243226.1 |
| | | NM_001243227.1 |
| | | NM_001243228.1 |
| | | NM_001243230.1 |
| | | NM_001243231.1 |
| | | NM_001243232.1 |
| | | NM_001243233.1 |
| | | NM_001243234.1 |
| | | NM_001243235.1 |
| | | NM_001243236.1 |
| | | NM_003199.2 |
| IGFBP6 | 3489 | NM_002178.2 |
| COL5A1 | 1289 | NM_000093.3 |
| ITGA3 | 3675 | NM_002204.2 |
| | | NM_005501.2 |
| NTM | 50863 | NM_001048209.1 |
| | | NM_001144058.1 |
| | | NM_001144059.1 |
| | | NM_016522.2 |
| LOC100130938 | 100130938 | |
| C12orf75 | 387882 | NM_001145199.1 |
| FBN2 | 2201 | NM_001999.3 |
| CRIM1 | 51232 | NM_016441.2 |
| TPM1 | 7168 | NM_000366.5 |
| | | NM_001018004.1 |
| | | NM_001018005.1 |
| | | NM_001018006.1 |
| | | NM_001018007.1 |
| | | NM_001018008.1 |
| | | NM_001018020.1 |
| COL6A2 | 1292 | NM_001849.3 |
| | | NM_058174.2 |
| | | NM_058175.2 |
| CCL2 | 6347 | NM_002982.3 |
| EFNB2 | 1948 | NM_004093.3 |
| IL1A | 3552 | NM_000575.3 |
| Sensitive | | |
| IGSF11 | 152404 | NM_001015887.1 |
| | | NM_152538.2 |
| FAM167B | 84734 | NM_032648.2 |
| MTUS1 | 57509 | NM_001001924.2 |
| | | NM_001001925.2 |
| | | NM_001001931.2 |
| | | NM_001166393.1 |
| | | NM_020749.4 |

TABLE 2-continued

| Human Gene | Entrez ID | Transcript IDs |
|---|---|---|
| GYG2 | 8908 | NM_001079855.1 |
| | | NM_001184702.1 |
| | | NM_001184703.1 |
| | | NM_001184704.1 |
| | | NM_003918.2 |
| GDF15 | 9518 | NM_004864.2 |
| LINC00518 | 221718 | |
| TYR | 7299 | NM_000372.4 |
| LRRK2 | 120892 | NM_198578.3 |
| ID4 | 3400 | NM_001546.3 |
| CMTM8 | 152189 | NM_178868.3 |
| KIAA0226L | 80183 | NM_025113.2 |
| C11orf96 | 387763 | NM_001145033.1 |
| D4S234E | 27065 | NM_001040101.1 |
| | | NM_014392.3 |
| SLC45A2 | 51151 | NM_001012509.2 |
| | | NM_016180.3 |
| TBC1D16 | 125058 | NM_001271844.1 |
| | | NM_001271845.1 |
| | | NM_001271846.1 |
| | | NM_019020.3 |
| TTYH2 | 94015 | NM_032646.5 |
| | | NM_052869.1 |
| LAMA1 | 284217 | NM_005559.3 |
| PMEL | 6490 | NM_001200053.1 |
| | | NM_001200054.1 |
| | | NM_006928.4 |
| PROS1 | 5627 | NM_000313.3 |
| PLA1A | 51365 | NM_001206960.1 |
| | | NM_001206961.1 |
| | | NM_015900.3 |
| KCNN2 | 3781 | NM_021614.2 |
| | | NM_170775.1 |
| ESRP1 | 54845 | NM_001034915.2 |
| | | NM_001122825.1 |
| | | NM_001122826.1 |
| | | NM_001122827.1 |
| | | NM_017697.3 |
| ST3GAL6 | 10402 | NM_001271142.1 |
| | | NM_001271145.1 |
| | | NM_001271146.1 |
| | | NM_001271147.1 |
| | | NM_001271148.1 |
| | | NM_006100.3 |
| DCT | 1638 | NM_001129889.1 |
| | | NM_001922.3 |
| TRIM63 | 84676 | NM_032588.3 |
| CITED1 | 4435 | NM_001144885.1 |
| | | NM_001144886.1 |
| | | NM_001144887.1 |
| | | NM_004143.3 |
| RAB38 | 23682 | NM_022337.2 |
| RXRG | 6258 | NM_001256570.1 |
| | | NM_001256571.1 |
| | | NM_006917.4 |
| TNFRSF14 | 8764 | NM_003820.2 |
| PLEKHH1 | 57475 | NM_020715.2 |
| CPN1 | 1369 | NM_001308.2 |
| PI15 | 51050 | NM_015886.3 |
| GNPTAB | 79158 | NM_024312.4 |
| GALNT3 | 2591 | NM_004482.3 |
| MREG | 55686 | NM_018000.2 |
| GPM6B | 2824 | NM_001001994.1 |
| | | NM_001001995.1 |
| | | NM_001001996.1 |
| | | NM_005278.3 |
| RRAGD | 58528 | NM_021244.4 |
| CAPN3 | 825 | NM_000070.2 |
| | | NM_024344.1 |
| | | NM_173087.1 |
| | | NM_173088.1 |
| | | NM_173089.1 |
| | | NM_173090.1 |

TABLE 2-continued

| Human Gene | Entrez ID | Transcript IDs |
|---|---|---|
| MLANA | 2315 | NM_005511.1 |
| RNF144A | 9781 | NM_014746.3 |
| MITF | 4286 | NM_000248.3 |
| | | NM_001184967.1 |
| | | NM_001184968.1 |
| | | NM_006722.2 |
| | | NM_198158.2 |
| | | NM_198159.2 |
| | | NM_198177.2 |
| | | NM_198178.2 |

Marker Expression

As used herein, dis-regulation of a marker (whether that be up-regulation or down-regulation) is defined relative to either a resistant or a sensitive cancer. For example, if a marker is up-regulated for example 4-fold in a resistant cell, this means that its expression level in a resistant cell (or population) is 4-fold higher than its expression in a sensitive cell (or population).

Up-regulation may mean detectable expression of a marker in a test sample (e.g., a cancer) where a control sample has undetectable expression of the marker. It may mean an increased level of expression of a marker in a test sample relative to a control sample that has detectable expression of the marker. In the latter case, the level of expression of up-regulated markers is greater than 1-fold, and may be 2-fold, 3-fold, 4-fold, or 5-fold higher than the resistant or sensitive population of cells, as described above.

As used herein, down-regulation of a marker is defined relative to a control. It may mean undetectable expression of a marker in a test sample (e.g., a cancer) where a control sample has detectable expression of the marker. It may mean a decreased level of expression of a marker in a test sample relative to a control sample that has detectable expression of the marker. In the latter case, the level of expression of down-regulated markers may be decreased by greater than 1-fold, and may be 1.5-fold, 2-fold, 3-fold, 4-fold, 5-fold, or more relative to the resistant or sensitive population of cells, as described cells.

MAPK Pathway

The mitogen-activated protein kinase (MAPK) cascade is a critical intracellular signaling pathway that regulates signal transduction in response to diverse extracellular stimuli, including growth factors, cytokines, and proto-oncogenes. Activation of this pathway results in transcription factor activation and alterations in gene expression, which ultimately lead to changes in cellular functions including cell proliferation, cell cycle regulation, cell survival, angiogenesis and cell migration. Classical MAPK signaling is initiated by receptor tyrosine kinases at the cell surface, however many other cell surface molecules are capable of activating the MAPK cascade, including integrins, heterotrimeric G-proteins, and cytokine receptors.

Ligand binding to a cell surface receptor, e.g., a receptor tyrosine kinase, typically results in phosphorylation of the receptor. The adaptor protein Grb2 associates with the phosphorylated intracellular domain of the activated receptor, and this association recruits guanine nucleotide exchange factors (GEFs) including SOS-I and CDC25 to the cell membrane. These particular GEFs interact with and activate the GTPase Ras. Common Ras isoforms include K-Ras, N-Ras, H-Ras and others. Following Ras activation, the serine/threonine kinase Raf (e.g., A-Raf, B-Raf or Raf-1) is recruited to the cell membrane through interaction with Ras. Raf is then phosphorylated. Raf directly activates MEK1 and MEK2 by phosphorylation of two serine residues at positions 217 and 221. Following activation, MEK1 and MEK2 phosphorylate tyrosine (Tyr-185) and threonine (Thr-183) residues in serine/threonine kinases Erk1 and Erk2, resulting in Erk activation. Activated Erk regulates many targets in the cytosol and also translocates to the nucleus, where it phosphorylates a number of transcription factors regulating gene expression. Erk kinase has numerous targets, including EIk-I, c-Ets1, c-Ets2, p90RSK1, MNK1, MNK2, MSK1, MSK2 and TOB. While the foregoing pathway is a classical representation of MAPK signaling, there is considerable cross talk between the MAPK pathway and other signaling cascades.

Aberrations in MAPK signaling have a significant role in cancer biology. Altered expression of Ras is common in many cancers, and activating mutations in Ras have also been identified. Such mutations are found in up to 30% of all cancers, and are especially common in pancreatic (90%) and colon (50%) carcinomas. In addition, activating Raf mutations have been identified in melanoma and ovarian cancer. The most common mutation, $BRAF^{V600E}$, results in constitutive activation of the downstream MAP kinase pathway and is required for melanoma cell proliferation, soft agar growth, and tumor xenograft formation. Based on these observations, certain MAPK pathway inhibitors have been targeted in various cancer therapies. However, it has also been observed that certain patients have or develop a resistance to certain of these therapies.

Expression Assays

Diagnostic, prognostic, and theranostic assays of the invention involve assaying gene copy, mRNA expression, protein expression and/or activity of one or more markers. The art is familiar with assays for copy number, mRNA expression levels, protein expression levels, and activity levels of the one or more markers (see, e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.).

Expression Level Analysis

The invention contemplates methods that involve measuring the mRNA or protein levels for one or more of the resistance and sensitivity markers provided herein and comparing such levels to control levels, including for example predetermined thresholds.

mRNA Assays

The art is familiar with various methods for analyzing mRNA levels. Examples of mRNA-based assays include but are not limited to oligonucleotide microarray assays, quantitative RT-PCR, Northern analysis, and multiplex bead-based assays.

Expression profiles of cells in a biological sample (e.g., blood or a tumor) can be carried out using an oligonucleotide microarray analysis. As an example, this analysis may be carried out using a commercially available oligonucleotide microarray or a custom designed oligonucleotide microarray comprising oligonucleotides for all or a subset of the transcripts described herein. The microarray may comprise any number of the transcripts, as the invention contemplates that elevated risk may be determined based on the analysis of single differentially expressed transcripts or a combination of differentially expressed transcripts. The transcripts may be those that are up-regulated in tumors carrying a germ-line risk marker (compared to a tumor that does not carry the germ-line risk marker), or those that are down-regulated in tumors carrying a germ-line risk marker (compared to a tumor that does not carry the germ-line risk marker), or a combination of these. The number of transcripts measured using the microarray therefore may be 1, 2, 3, 4, 5, 6, 7, 8, 9, or more transcripts encoded by a gene in Table 2. It is to be understood that such arrays may however also comprise positive and/or negative control transcripts such as housekeeping genes that can be used to determine if the array has been degraded and/or if the sample has been degraded or contaminated. The art is familiar with the construction of oligonucleotide arrays.

Commercially available gene expression systems include Affymetrix GeneChip microarrays as well as all of Illumina standard expression arrays, including two GeneChip 450 Fluidics Stations and a GeneChip 3000 Scanner, Affymetrix High-Throughput Array (HTA) System composed of a GeneStation liquid handling robot and a GeneChip HT Scanner providing automated sample preparation, hybridization, and scanning for 96-well Affymetrix PEGarrays. These systems can be used in the cases of small or potentially degraded RNA samples. The invention also contemplates analyzing expression levels from fixed samples (as compared to freshly isolated samples). The fixed samples include formalin-fixed and/or paraffin-embedded samples. Such samples may be analyzed using the whole genome Illumina DASL assay. High-throughput gene expression profile analysis can also be achieved using bead-based solutions, such as Luminex systems.

Other mRNA detection and quantitation methods include multiplex detection assays known in the art, e.g., xMAP® bead capture and detection (Luminex Corp., Austin, Tex.).

Another exemplary method is a quantitative RT-PCR assay which may be carried out as follows: mRNA is extracted from cells in a biological sample (e.g., blood or a tumor) using the RNeasy kit (Qiagen). Total mRNA is used for subsequent reverse transcription using the SuperScript III First-Strand Synthesis SuperMix (Invitrogen) or the SuperScript VILO cDNA synthesis kit (Invitrogen). 5 µl of the RT reaction is used for quantitative PCR using SYBR Green PCR Master Mix and gene-specific primers, in triplicate, using an ABI 7300 Real Time PCR System.

mRNA detection binding partners include oligonucleotide or modified oligonucleotide (e.g. locked nucleic acid) probes that hybridize to a target mRNA. Probes may be designed using the sequences associated with the sequence identifiers listed in Table 2. Methods for designing and producing oligonucleotide probes are well known in the art (see, e.g., U.S. Pat. No. 8,036,835; Rimour et al. GoArrays: highly dynamic and efficient microarray probe design. Bioinformatics (2005) 21 (7): 1094-1103; and Wernersson et al. Probe selection for DNA microarrays using OligoWiz. Nat Protoc. 2007; 2(11):2677-91).

Protein Assays

The art is familiar with various methods for measuring protein levels. Protein levels may be measured using protein-based assays such as but not limited to immunoassays, Western blots, Western immunoblotting, multiplex bead-based assays, and assays involving aptamers (such as SOMAmer™ technology) and related affinity agents.

A brief description of an exemplary immunoassay is provided here. A biological sample is applied to a substrate having bound to its surface protein-specific binding partners (i.e., immobilized protein-specific binding partners). The protein-specific binding partner (which may be referred to as a "capture ligand" because it functions to capture and immobilize the protein on the substrate) may be an antibody or an antigen-binding antibody fragment such as Fab, F(ab)2, Fv, single chain antibody, Fab and sFab fragment, F(ab')2, Fd fragments, scFv, and dAb fragments, although it is not so limited. Other binding partners are described herein. Protein present in the biological sample bind to the capture ligands, and the substrate is washed to remove unbound material. The substrate is then exposed to soluble protein-specific binding partners (which may be identical to the binding partners used to immobilize the protein). The soluble protein-specific binding partners are allowed to bind to their respective proteins immobilized on the substrate, and then unbound material is washed away. The substrate is then exposed to a detectable binding partner of the soluble protein-specific binding partner. In one embodiment, the soluble protein-specific binding partner is an antibody having some or all of its Fc domain. Its detectable binding partner may be an anti-Fc domain antibody. As will be appreciated by those in the art, if more than one protein is being detected, the assay may be configured so that the soluble protein-specific binding partners are all antibodies of the same isotype. In this way, a single detectable binding partner, such as an antibody specific for the common isotype, may be used to bind to all of the soluble protein-specific binding partners bound to the substrate.

It is to be understood that the substrate may comprise capture ligands for one or more proteins, including two or more, three or more, four or more, five or more, etc. up to and including all the proteins encoded by the resistance and sensitivity markers provided by the invention.

Other examples of protein detection and quantitation methods include multiplexed immunoassays as described for example in U.S. Pat. Nos. 6,939,720 and 8,148,171, and published US Patent Application No. 2008/0255766, and protein microarrays as described for example in published US Patent Application No. 2009/0088329.

Protein detection binding partners include protein-specific binding partners. Protein-specific binding partners can be generated using sequences associated with the sequence identifiers listed in Table 2. In some embodiments, binding partners may be antibodies. As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and dAb fragments) as well as complete antibodies. Methods for making antibodies and antigen-binding fragments are well known in the art (see, e.g. Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609).

Binding partners also include non-antibody proteins or peptides that bind to or interact with a target protein, e.g., through non-covalent bonding. For example, if the protein is a ligand, a binding partner may be a receptor for that ligand. In another example, if the protein is a receptor, a binding partner may be a ligand for that receptor. In yet another example, a binding partner may be a protein or peptide known to interact with a protein. Methods for producing proteins are well known in the art (see, e.g. Sambrook et al, "Molecular Cloning: A Laboratory Manual" (2nd Ed.), Cold Spring Harbor Laboratory Press (1989) and Lewin, "Genes IV", Oxford University Press, New York, (1990)) and can be used to produce binding partners such as ligands or receptors.

Binding partners also include aptamers and other related affinity agents. Aptamers include oligonucleic acid or peptide molecules that bind to a specific target. Methods for producing aptamers to a target are known in the art (see, e.g., published US Patent Application No. 2009/0075834, U.S. Pat. Nos. 7,435,542, 7,807,351, and 7,239,742). Other examples of affinity agents include SOMAmer™ (Slow Off-rate Modified Aptamer, SomaLogic, Boulder, Colo.) modified nucleic acid-based protein binding reagents.

Binding partners also include any molecule capable of demonstrating selective binding to any one of the target proteins disclosed herein, e.g., peptoids (see, e.g., Reyna J Simon et al., "Peptoids: a modular approach to drug discovery" Proceedings of the National Academy of Sciences USA, (1992), 89(20), 9367-9371; U.S. Pat. No. 5,811,387; and M. Muralidhar Reddy et al., Identification of candidate IgG biomarkers for Alzheimer's disease via combinatorial library screening. Cell 144, 132-142, Jan. 7, 2011).

Copy Number and Activity Levels

Copy number can be measured, for example, using sequencing, fluorescence in situ hybridization (FISH) or a Southern blot.

Methods for measuring a marker activity are also known in the art and commercially available (see, e.g., enzyme and protein activity assays from Invitrogen, Piercenet, AbCam, EMD Millipore, or Sigma Aldrich). Non-limiting examples of assays for measuring marker activity include western blot, enzyme-linked immunosorbent assay (ELISA), fluorescent activated cell sorting (FACS), luciferase or chloramphenicol acetyl transferase reporter assay, protease colorimetric assay, immunoprecipitation (including Chromatin-IP), PCR, qPCR, or fluorescence resonance energy transfer.

Non-limiting examples of marker activities include phosphorylation (kinase or phosphotase activity), ubiquitination, SUMOylation, Neddylation, cytoplasmic or nuclear localization, binding to a binding partner (such as a protein, DNA, RNA, ATP, or GTP), transcription, translation, post-translation modification (such as glycosylation, methylation, or acetylation), chromatin modification, proteolysis, receptor activation or inhibition, cyclic AMP activation or inactivation, GTPase activation or inactivation, electron transfer, hydrolysis, or oxidation.

Marker activity may be measured indirectly. For example, if a marker must be phosphorylated or dephosphorylated before becoming active, a phosphorylation level of the marker may indicate an activity level.

Detectable Labels

Detectable binding partners may be directly or indirectly detectable. A directly detectable binding partner may be labeled with a detectable label such as a fluorophore. An indirectly detectable binding partner may be labeled with a moiety that acts upon (e.g., an enzyme or a catalytic domain) or a moiety that is acted upon (e.g., a substrate) by another moiety in order to generate a detectable signal. Exemplary detectable labels include, e.g., enzymes, radioisotopes, haptens, biotin, and fluorescent, luminescent and chromogenic substances. These various methods and moieties for detectable labeling are known in the art.

Controls

The control may be an expression level in a tissue, subject, or a population of subjects, or a cell line.

It is to be understood that the methods provided herein do not require that a control level be measured every time a subject is tested. Rather, it is contemplated that control levels may be obtained and recorded and that any test level is compared to such a pre-determined level or identity (or threshold).

Devices

Other aspects of the invention relate to devices. In some embodiments, the device comprises a sample inlet and a substrate, wherein the substrate comprises one or more binding partners for one or more markers as described herein. In some embodiments, the device is a microarray.

It is to be understood that the device may comprise binding partners for any combination of markers described herein or that can be contemplated by one of ordinary skill in the art based on the teachings provided herein.

The device may also comprise binding partners for one or more control markers. The control markers may be positive control markers (e.g., to ensure the device has maintained its integrity) and/or negative control markers (e.g., to identify contamination or to ensure the device has maintained its specificity). The nature of the control markers will depend in part on the nature of the biological sample.

The device may comprise binding partners for 1-150, 1-100, 1-50, 1-20, 1-10, 1-5, 2-150, 2-100, 2-50, 2-20, 2-10, 2-5, 3-150, 3-100, 3-50, 3-20, 3-10, 3-5, 4-150, 4-100, 4-50, 4-20, 4-10, 5-150, 5-100, 5-50, 5-20, 1-150, 1-100, 1-50, 1-20, 10-150, 10-100, 10-50, 10-20, 50-150, 50-100, or 100-150 of the markers recited herein.

The binding partners may be antibodies, antigen-binding antibody fragments, receptors, ligands, aptamers, nucleotides and the like, provided they bind selectively to the marker being tested and do not bind appreciably to any other marker that may be present in the biological sample loaded onto the device.

The binding partners may be provided on the substrate in a predetermined spatial arrangement. A substrate, as used herein in this context, refers to a solid support to which marker-specific binding partners may be bound. The substrate may be paper or plastic (e.g., polystyrene) or some other material that is amenable to the marker measurement. The substrate may have a planar surface although it is not so limited. In some instances, the substrate is a bead or sphere.

The art is familiar with diagnostic devices and reference can be made to U.S. Pat. Nos. 7,897,356 and 7,323,143, and published US Patent Application Publication No. US 2008/0267999, and Martinez et al. PNAS, 2008, 105 (50): 19606-19611, all of which are incorporated herein by reference in their entirety.

Diagnostic/Prognostic/Theranostic Methods

The invention therefore provides methods of detecting the presence of one and preferably more than one (in the form of a signature) predictive, diagnostic or prognostic markers in a sample (e.g., a biological sample from a cancer patient, preferably from a patient having melanoma or other cancer being treated with or being considered for treatment with a MAPK pathway inhibitor). A variety of screening methods known to one of skill in the art may be used to detect the presence and the level of the markers in the sample including DNA, RNA and protein detection.

In some embodiments, the subject may have or may be at risk of developing intrinsic or acquired resistance to MAP kinase targeted therapies, including RAF inhibitors, MEK inhibitors, and/or ERK inhibitors. The subject may or may be currently receiving a MAPK pathway inhibitor. For example, the subject may have a resistance to RAF inhibitors, such as PLX4720 and/or PLX4032. In some embodiments, the subject may have resistance to a MEK inhibitor, such as AZD6244. In some embodiments, the subject may have resistance to an ERK inhibitor, such as VTX11e. The resistance may be intrinsic or acquired. In some embodiments, the resistance is intrinsic resistance.

As used herein, "resistance" includes a non-responsiveness or decreased responsiveness in a subject to treatment with an inhibitor. Non-responsiveness or decreased responsiveness may include an absence or a decrease of the benefits of treatment, such as a decrease or cessation of the relief, reduction or alleviation of at least one symptom of the disease in the subject. For example, in a subject having a cancer that in not resistant to (i.e., sensitive to) a MAPK pathway inhibitor, administration of the inhibitor to the subject may result in a reduction of tumor burden or complete eradication of the cancer. On the other hand, in a subject having a cancer resistant to a MAPK pathway inhibitor, administration of the inhibitor to the subject may result in no reduction of tumor burden (or a smaller reduction in tumor burden than would be observed with a sensitive cancer) and/or no eradication of the cancer.

As used herein, "intrinsic resistance" describes a cancer that is naturally resistant to an inhibitor. As used herein, "acquired resistance" describes a cancer that develops resistance to an inhibitor after administration of the inhibitor to the subject.

Identification of the signatures of the invention in a subject may assist a physician or other medical professional in determining a treatment protocol for the subject. For example, in a subject having a cancer with a resistant signature, the physician may treat the subject with a different therapy than that which would have otherwise been prescribed. In a subject having a cancer with a sensitive signature, the physician may treat the subject with a MAPK pathway inhibitor.

Inhibitors

Aspects of the invention relate to MAPK pathway inhibitors. MAPK pathway inhibitors include RAF, MEK, and ERK inhibitors.

The inhibitor may target the gene, mRNA expression, protein expression, and/or activity, in all instances reducing the level and/or activity, in whole or in part, of the target of the inhibitor (e.g., RAF, MEK, or ERK).

Non-limiting examples of RAF inhibitors include RAF265, sorafenib, dabrafenib (GSK2118436), SB590885, PLX 4720, PLX4032, GDC-0879 and/or ZM 336372. By way of non-limiting example, exemplary RAF inhibitors are shown in Table 3 and thereafter.

TABLE 3

Exemplary RAF Inhibitors (9 exemplary compounds)

Compound 1, Name: RAF265, CAS No.: 927880-90-8

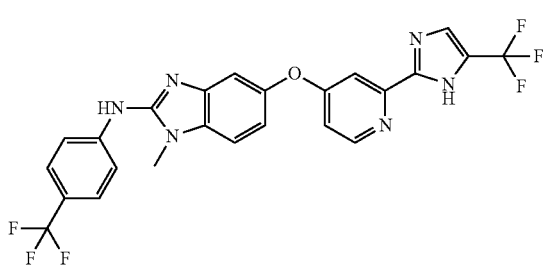 [SMILES: Cn1c(Nc2ccc(C(F)(F)F)cc2)nc2cc(Oc3ccnc(-c4ncc(C(F)(F)F)[nH]4)c3)ccc21]

Compound 2, Name: Sorafenib Tosylate (Nexavar, Bay 43-9006), CAS No.: 475207-59-1

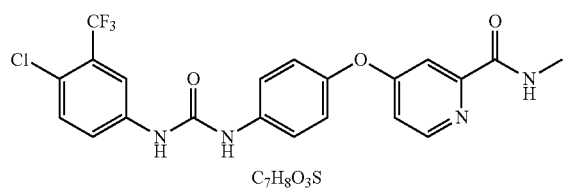

$C_7H_8O_3S$

Compound 3, Name: Sorafenib 4-[4-[[4-chloro-3-(trifluoromethyl)phenyl]carbamoylamino]phenoxy]-N-methyl-pyridine-2-carboxamide, CAS No.: 284461-73-0

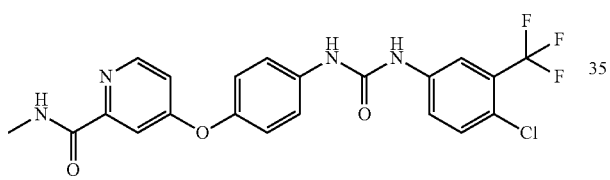

Compound 4, Name: SB590885

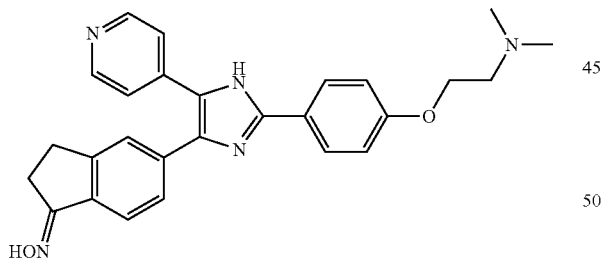

Compound 5, Name: PLX4720, CAS No.: 918505-84-7

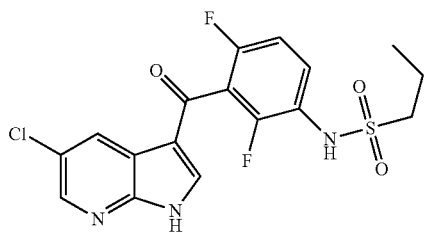 [SMILES: CCCS(=O)(=O)Nc1ccc(F)c(C(=O)c2c[nH]c3ncc(Cl)cc23)c1F]

Compound 6, Name: PLX4032, CAS No.: 1029872-54-5

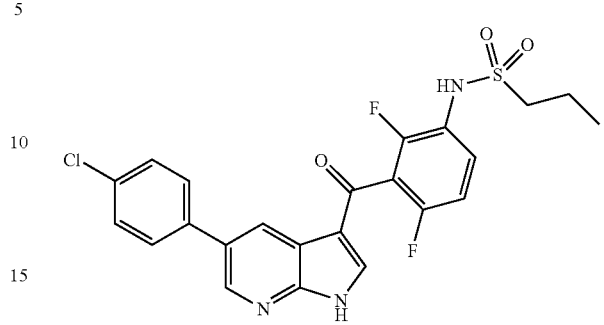

Compound 7, Name: GDC-0879, CAS No.: 905281-76-7

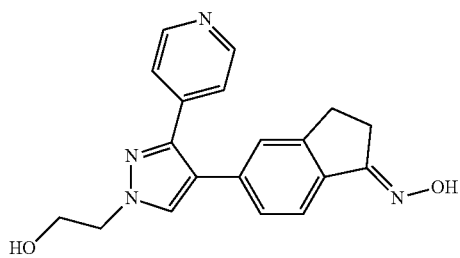 [SMILES: OCCn1cc(-c2ccc3c(c2)CC/C3=N\O)c(-c2ccncc2)n1]

Compound 8, Name: ZM 336372, CAS No.: 208260-29-1

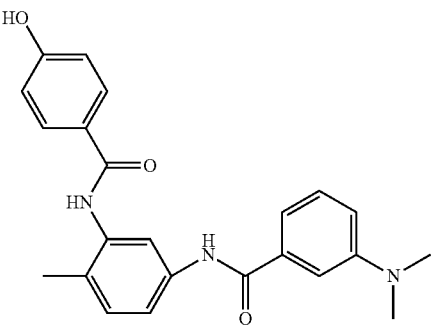 [SMILES: Cc1ccc(NC(=O)c2cccc(N(C)C)c2)cc1NC(=O)c1ccc(O)cc1]

Compound 9, Name: Dabrafenib, CAS No.: 1195765-45-7

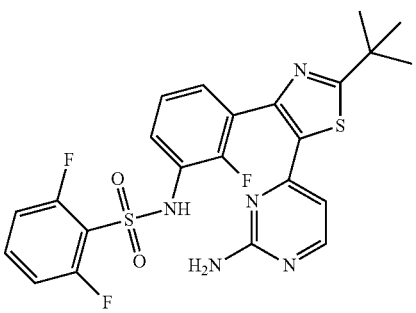 [SMILES: CC(C)(C)c1nc(-c2cccc(NS(=O)(=O)c3c(F)cccc3F)c2F)c(-c2ccnc(N)n2)s1]

Additional examples of RAF inhibitors therefore include PLX4720, PLX4032, BAY 43-9006 (Sorafenib), ZM 336372, RAF 265, AAL-881, LBT-613, or CJS352 (NVP-AAL881-NX (hereafter referred to as AAL881) and NVP-LBT613-AG-8 (LBT613) are isoquinoline compounds (Novartis, Cambridge, Mass.). Additional exemplary RAF inhibitors useful for combination therapy include pan-RAF inhibitors, inhibitors of B-RAF, inhibitors of A-RAF, and inhibitors of RAF-1. In exemplary embodiments RAF inhibitors useful for combination therapy include PLX4720, PLX4032, BAY 43-9006 (Sorafenib), ZM 336372, RAF 265, AAL-881, LBT-613, and CJS352. Exemplary RAF inhibitors further include the compounds set forth in PCT Publication No. WO/2008/028141, the specific teachings of which are incorporated herein by reference. Exemplary RAF inhibitors additionally include the quinazolinone derivatives described in PCT Publication No. WO/2006/024836, and the pyridinylquinazolinamine derivatives described in PCT Publication No. WO/2008/020203, the specific inhibitor teachings of which are incorporated herein by reference.

Non-limiting examples of MEK inhibitors include, AZD6244, CI-1040/PD184352, PD318088, PD98059, PD334581, RDEA119, 6-Methoxy-7-(3-morpholin-4-yl-propoxy)-4-(4-phenoxy-phenylamino)-quinoline-3-carbonitrile and 4-[3-Chloro-4-(1-methyl-1H-imidazol-2-ylsulfanyl)-phenylamino]-6-methoxy-7-(3-morpholin-4-yl-propoxy)-quinoline-3-carbonitrile, trametinib (GSK1120212), and/or ARRY-438162. By way of non-limiting example, exemplary MEK inhibitors are shown in Table 4 and thereafter.

TABLE 4

Exemplary MEK Inhibitors (9 exemplary compounds)

Compound 1, Name: CI-1040/PD184352, CAS No.: 212631-79-3

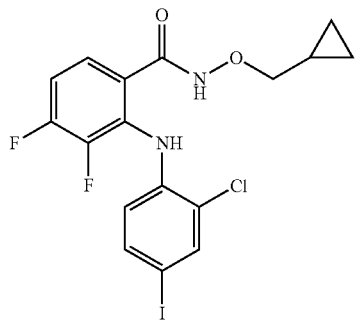 [SMILES: O=C(NOCC1CC1)c1ccc(F)c(F)c1Nc1ccc(I)cc1Cl]

Compound 2, Name: AZD6244, CAS No.: 606143-52-6

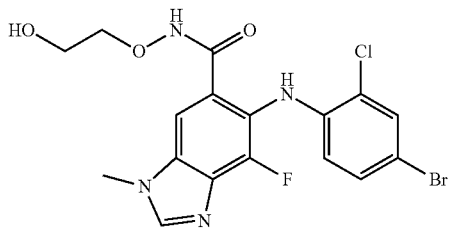 [SMILES: Cn1cnc2c(F)c(Nc3ccc(Br)cc3Cl)c(C(=O)NOCCO)cc21]

Compound 3, Name: PD318088, CAS No.: 391210-00-7

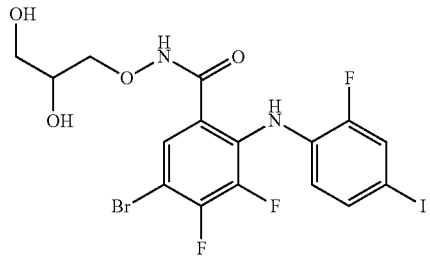 [SMILES: O=C(NOCC(O)CO)c1cc(Br)c(F)c(F)c1Nc1ccc(I)cc1F]

TABLE 4-continued

Exemplary MEK Inhibitors (9 exemplary compounds)

Compound 4, Name: PD98059, CAS No.: 167869-21-8

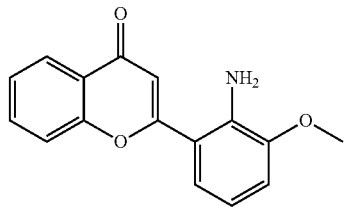 [SMILES: COc1cccc(-c2cc(=O)c3ccccc3o2)c1N]

Compound 5, Name: PD334581

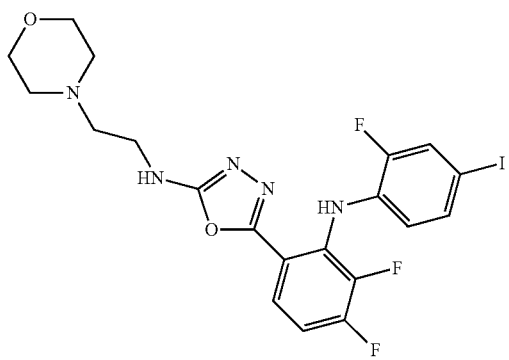 [SMILES: Fc1cc(I)ccc1Nc1c(-c2nnc(NCCN3CCOCC3)o2)ccc(F)c1F]

Compound 6, Name: RDEA119 (N-[3,4-difluoro-2-[(2-fluoro-4-iodophenyl)amino]-6-methoxyphenyl]-1-[(2R)-2,3-dihydroxypropyl]-Cyclopropanesulfonamide), CAS No.: 923032-38-6

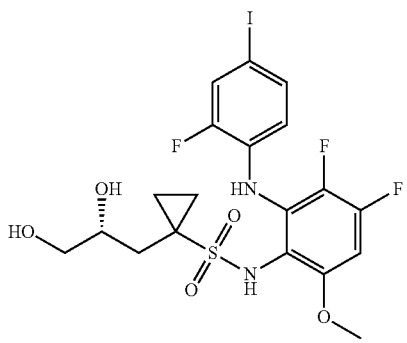 [SMILES: COc1cc(F)c(F)c(Nc2ccc(I)cc2F)c1NS(=O)(=O)C1(C[C@@H](O)CO)CC1]

Compound 7, Name: 6-Methoxy-7-(3-morpholin-4-yl-propoxy)-4-(4-phenoxy-phenylamino)-quinoline-3-carbonitrile

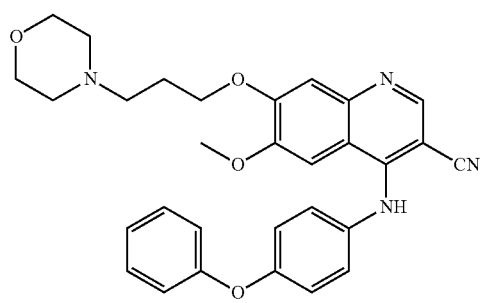 [SMILES: COc1cc2c(Nc3ccc(Oc4ccccc4)cc3)c(C#N)cnc2cc1OCCCN1CCOCC1]

TABLE 4-continued

Exemplary MEK Inhibitors (9 exemplary compounds)

Compound 8, Name: 4-[3-Chloro-4-(1-methyl-1H-imidazol-2-ylsulfanyl)-phenylamino]-6-methoxy-7-(3-morpholin-4-yl-propoxy)-quinoline-3-carbonitrile

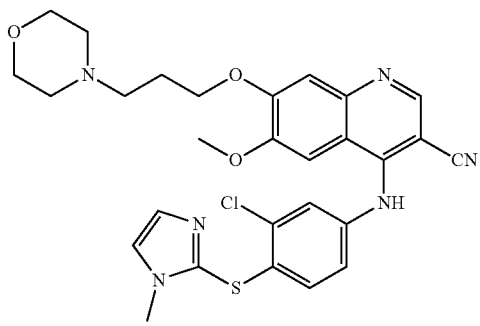 [SMILES: COc1cc2c(Nc3ccc(Sc4nccn4C)c(Cl)c3)c(C#N)cnc2cc1OCCCN1CCOCC1]

Compound 9, Name: Trametinib, CAS No.: 871700-17-3

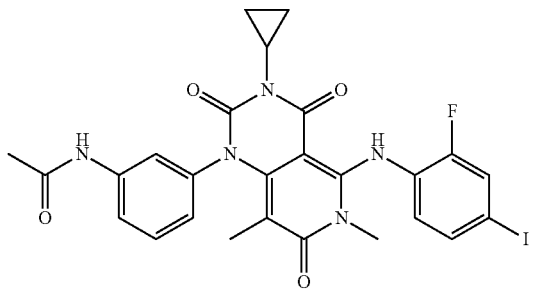 [SMILES: CC(=O)Nc1cccc(-n2c(=O)n(C3CC3)c(=O)c3c(Nc4ccc(I)cc4F)n(C)c(=O)c(C)c32)c1]

Additional MEK inhibitors include the compounds described in the following patent publications, the specific inhibitor teachings of which are incorporated herein by reference: WO 2008076415, US 20080166359, WO 2008067481, WO 2008055236, US 20080188453, US 20080058340, WO 2007014011, WO 2008024724, US 20080081821, WO 2008024725, US 20080085886, WO 2008021389, WO 2007123939, US 20070287709, WO 2007123936, US 20070287737, US 20070244164, WO 2007121481, US 20070238710, WO 2007121269, WO 2007096259, US 20070197617, WO 2007071951, EP 1966155, IN 2008MN01163, WO 2007044084, AU 2006299902, CA 2608201, EP 1922307, EP 1967516, MX 200714540, IN 2007DN09015, NO 2007006412, KR 2008019236, WO 2007044515, AU 2006302415, CA 2622755, EP 1934174, IN 2008DN02771, KR 2008050601, WO 2007025090, US 20070049591, WO 2007014011, AU 2006272837, CA 2618218, EP 1912636, US 20080058340, MX 200802114, KR 2008068637, US 20060194802, WO 2006133417, WO 2006058752, AU 2005311451, CA 2586796, EP 1828184, JP 2008521858, US 20070299103, NO 2007003393, WO 2006056427, AU 2005308956, CA 2587178, EP 1838675, JP 2008520615, NO 2007003259, US 20070293544, WO 2006045514, AU 2005298932, CA 2582247, EP 1802579, CN 101065358, JP 2008517024, IN 2007DN02762, MX 200704781, KR 2007067727, NO 2007002595, JP 2006083133, WO 2006029862, US 20060063814, U.S. Pat. No. 7,371,869, AU 2005284293, CA 2579130, EP 1791837, CN 101023079, JP 2008513397, BR 2005015371, KR 2007043895, MX 200703166, IN 2007CN01145, WO 2006034034, AU 2005276974, CA 2578283, US 20060079526, EP 1799656, CN 101044125, JP 2008510839, MX 200702208, IN 2007DN02041, WO 2006018188, AU 2005274390, CA 2576599, EP 1781649, CN 101006085, JP 2008509950, BR 2005014515, AT 404556, US 20060041146, MX 200701846, IN 2007CN00695, KR 2007034635, WO 2006011466, AU 2005265769, CA 2575232, EP 1780197, BR 2005013750, JP 4090070, MX 200700736, CN 101124199, KR 2007041752, IN 2007DN01319, WO 2005121142, AU 2005252110, CA 2569850, US 20060014768, U.S. Pat. No. 7,378,423, EP 1761528, CN 101006086, AT 383360, BR 2005011967, JP 2008501631, EP 1894932, ES 2297723, MX 2006PA14478, NO 2007000155, IN 2007CN00102, KR 2007034581, HK 1107084, JP 2008201788, US 20050256123, US 20050250782, US 20070112038, US 20050187247, WO 2005082891, WO 2005051302, AU 2004293019, CA 2546353, US 20050130943, US 20050130976, US 20050153942, EP 1689233, JP 2007511615, WO 2005051301 AU 2004293018, CA 2545660, US 20050130943, US 20050130976, US 20050153942, EP 1682138, BR 2004016692, CN 1905873, JP 2007511614, MX 2006PA05657, IN 2006DN03183, NO 2006002692, KR 2007026343, WO 2005028426, EP 1674452, US 20070105859, US 20050054701, U.S. Pat. No. 7,230,099, US 20050049419, U.S. Pat. No. 7,144,907, AU 2004270699, CA 2537321, WO 2005023759, EP 1673339, BR 2004014111, CN 1874769, JP 2007504241, JP 4131741, US 20060030610, MX 2006PA02466, NO 2006001506, US 20050049419, U.S. Pat. No. 7,144,907, US 20050054701, U.S. Pat. No. 7,230,099, AU 2004270699, CA 2537321, WO 2005023759, EP 1673339, BR 2004014111, CN 1874769, JP 2007504241, JP 4131741 US 20060030610, MX 2006PA02466, IN 2006DN01661, NO 2006001506, US 20060189808, US 20060189649, U.S. Pat. No. 7,271,178, US 20060189668, US 20050049276, WO 2005009975, CA 2532067, EP 1651214, BR 2004012851, JP 2006528621, US 20050026970, U.S. Pat. No. 7,160,915, MX 2006PA00921, WO 2005007616, US 20050059710, WO 2005000818, US 20050026964, U.S. Pat. No. 7,273,877, WO 2004056789, US 20050004186, CA 2509405, AU 2003286306, EP 1578736, BR 2003017254, JP 2006516967, MX 2005PA06803, WO 2004044219, AU 2003291268, WO 2004041811, AU 2003278369, EP 1575943, JP 2006508944, US 20050282856, U.S. Pat. No. 7,173,136, US 20070191346, WO 2004041185, AU 2003287366, US 20060270643, WO 2004030620, AU 2003275282, US 20040092514, U.S. Pat. No. 7,232,826, EP 1545529, US 20040039037, U.S. Pat. No. 6,989,451, WO 2003077855, CA 2478534, AU 2003220202, US 20030216460, EP 1482944, CN 1652792, JP 2005526076, RU 2300528, BR 2003006016, MX 2004PA08894, US 20060106225, WO 2003062191, CA 2473545, EP 1467968, BR 2003007060, JP 2005515253, TW 592692, US 20040006245, U.S. Pat. No. 6,891,066, MX 2004PA05527, US 20050137263, U.S. Pat. No. 7,078,438, WO 2003062189, CA 2472367, EP 1467965, BR 2003007071, JP 2005515251, US 20030232889, U.S. Pat. No. 6,770,778, MX 2004PA05528, WO 2003047585, AU 2002347360, WO 2003047583, AU 2002365665, WO 2003047523, CA 2466762, AU 2002365899, US 20030125359, U.S. Pat. No. 7,307,071, JP 2005526008, EP 1578346, WO 2003035626, CA 2463101, AU 2002359291, EP 1438295, JP 2005508972, US 20050054706, U.S. Pat. No. 7,253,199, US 20070293555, AU 2008202731, U.S. Pat. No. 6,506,798, WO 9901421, WO 2000041994, U.S. Pat. No. 6,310,060, WO 2002006213, CA 2416685, AU 2001073498, BR 2001012584, HU 2003002781, JP 2004504294, JP 3811775, EE 200300030, NZ 524120, AU 2001273498, IN 2003MN00028, NO 2003000249, KR 773621, MX 2003PA00591, HR 2003000083, BG 107564, ZA 2003000348, US 20040054172, U.S. Pat. No. 6,960,614, HK 1055943, US 20050176820, U.S. Pat. No. 7,411,001, WO 2000042029, JP 2000204077, CA 2355374, EP 1144394, BR 9916896, TR 200102029, HU 2001005092, JP 2002534515, EE 200100374, NZ 513432, AT 302761, ES 2249060, ZA 2001005219, MX 2001PA06659, IN 2001MN00785, NO 2001003451, HR 2001000525, BG 105801, U.S. Pat. No. 6,545,030, HK 1042488, US 20030004193, WO 2000042022, JP 2000204079, CA 2355470, EP 1144385, BR 9916904, TR 200102030, HU 2001005113, EE 200100373, JP 2002534510, NZ 513433, AT 302193, ES 2247859, MX 2001PA06568, ZA 2001005224, IN 2001MN00786, U.S. Pat. No. 6,469,004, NO 2001003452, HR 2001000524, BG 105800, WO 2000042003, JP 2000212157, CA 2349832, EP 1144371, BR 9916885, AT 309205, ES 2252996, MX 2001PA04332, U.S. Pat. No. 6,440,966, US 20030092748, U.S. Pat. No. 6,750,217, WO 2000042002, JP 2000204075, CA 2349467, EP 1144372, BR 9916894, JP 2002534497, AT 311363, ES 2251851, MX 2001PA04331, U.S. Pat. No. 6,455,582, US 20030045521, U.S. Pat. No. 6,835,749, WO 2000037141, CA 2352326, BR 9916839, EP 1140291, TR 200101871, HU 2001004844, JP 2002532570, EE 200100339, NZ 512859, AT 310567, ES 2253928, ZA 2001004277, MX 2001PA05476, IN 2001MN00673, NO 2001003099, HR 2001000473, BG 105715, US 20040171632, GB 2323845, WO 9901426, CA 2290506, AU 9882627, AU 757046, EP 993439, BR 9810366, NZ 501276, HU 2000003731, JP 2002511092, AT 277895, IL 132840, PT 993439, ES 2229515, TW 396149, ZA 9805728, MX 9910649, NO 9906491, NO 315271, US 20030078428, U.S. Pat. No. 6,821,963, US 20050049429, US 20060052608, U.S. Pat. No. 7,169,816, WO 9901421, CA 2290509, AU 9882626, AU 756586, EP 993437, BR 9810385, JP 2002509536, NZ 501277, AT 344791, ES 2274572, TW 221831, ZA 9805726, MX 9910556, U.S. Pat. Nos. 6,310,060, 6,506,798, US 20020022647, U.S. Pat. No. 6,492,363, US 20030149015, and U.S. Pat. No. 7,019,033.

Non-limiting examples of ERK inhibitors include VTX11e, AEZS-131 (Aeterna Zentaris), PD98059, FR180204, and/or FR148083. By way of non-limiting example, exemplary MEK inhibitors are shown in Table 5 and thereafter.

TABLE 5

Exemplary ERK Inhibitors (4 exemplary compounds)

Compound 1, Name: VTX11e

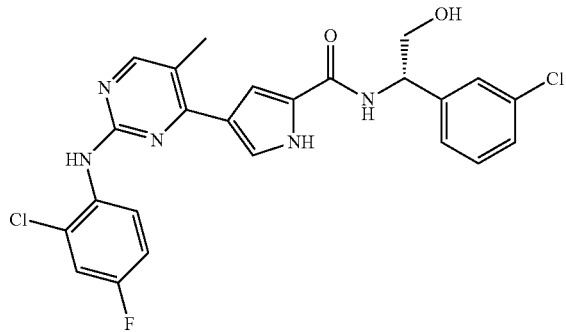 [SMILES: Cc1cnc(Nc2ccc(F)cc2Cl)nc1-c1c[nH]c(C(=O)N[C@H](CO)c2cccc(Cl)c2)c1]

TABLE 5-continued

Exemplary ERK Inhibitors (4 exemplary compounds)

Compound 2, Name: PD98059, CAS No.: 167869-21-8

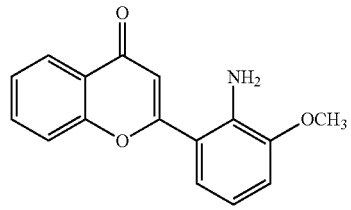 [SMILES: COc1cccc(-c2cc(=O)c3ccccc3o2)c1N]

Compound 3, Name: FR180204, CAS No.: 865362-74-9

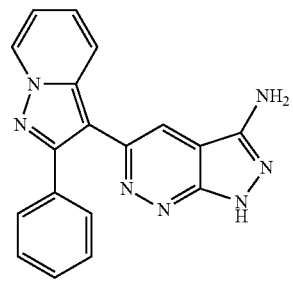 [SMILES: Nc1n[nH]c2nnc(-c3c(-c4ccccc4)nn4ccccc34)cc12]

Compound 4, Name: FR148083 (5Z-7-oxozeaenol), CAS No.: 253863-19-3

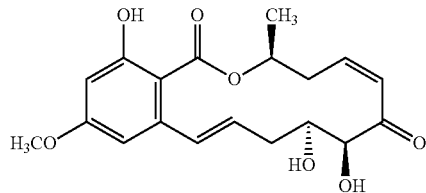 [SMILES: COc1cc(O)c2c(c1)/C=C/C[C@H](O)[C@H](O)C(=O)/C=C\C[C@H](C)OC2=O]

Additional ERK inhibitors include the compounds described in the following patents and patent publications, the specific inhibitor teachings of which are incorporated herein by reference: US 20120214823, US20070191604, US20090118284, US20110189192, U.S. Pat. No. 6,528,509, EP2155722A1, and EP2170893A1.

In some embodiments, two MAPK pathway inhibitors may be used in combination, for example, wherein one of a first of the two MAPK pathway inhibitors is a RAF inhibitor and a second of the two MAPK pathway inhibitors is a MEK inhibitor. In some embodiments, the first inhibitor is dabrafenib and the second inhibitor is trametinib.

Treatment Methods

The term "treat", "treated," "treating" or "treatment" is used herein to mean to relieve, reduce or alleviate at least one symptom of a disease in a subject. For example, treatment can be diminishment of one or several symptoms of a disorder or complete eradication of a disorder, such as cancer. Within the meaning of the present invention, the term "treat" also denote to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the disease is associated with a cancer.

The term "subject" or "patient" is intended to include animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats, and transgenic non-human animals. In certain embodiments, the subject is a human, e.g., a human having, at risk of having, or potentially capable of having cancer.

The term "cancer" is used herein to mean malignant solid tumors as well as hematological malignancies.

In particularly important embodiments, the cancer is one that would have been treated using a MAPK pathway inhibitor. In some instances, the cancer is melanoma. The melanoma may be metastatic melanoma.

The cancer may be associated with a mutation in the B-RAF gene. These cancers include melanoma, breast cancer, colorectal cancers, glioma, lung cancer, ovarian cancer, sarcoma and thyroid cancer. The cancer may be a BRAF mutant melanoma. In some embodiments, the mutation in a B-RAF gene is V600E.

Additional examples of such tumors include but are not limited to leukemias, lymphomas, myelomas, carcinomas, metastatic carcinomas, sarcomas, adenomas, nervous system cancers and genitourinary cancers, specific examples of which include but are not limited to adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

Aspects of the invention relate to treatment of a subject based on the levels of markers described herein. In some embodiments, a subject with cancer identified as being sensitive or likely to be sensitive to a MAPK pathway inhibitor is treated with a MAPK inhibitor. In some embodiments, a subject with cancer identified as being resistant or likely to be resistant to a MAPK pathway inhibitor is treated with a non-MAPK inhibitor therapy. In some embodiments, a subject with cancer identified as being resistant or likely to be resistant to a MAPK pathway inhibitor is treated with a MAPK pathway inhibitor in combination with another therapeutic agent.

Other methods of the invention comprise administration of a first inhibitor and a second inhibitor. The designation of "first" and "second" inhibitors is used to distinguish between the two and is not intended to refer to a temporal order of administration of the inhibitors.

The first inhibitor may be a RAF inhibitor. The RAF inhibitor may be a pan-RAF inhibitor or a selective RAF inhibitor. Pan-RAF inhibitors include but are not limited to RAF265, sorafenib, and SB590885. In some embodiments, the RAF inhibitor is a B-RAF inhibitor. In some embodiments, the selective RAF inhibitor is PLX4720, PLX4032, Dabrafenib, or GDC-0879-A. Other RAF inhibitors are provided herein.

The first inhibitor may be a MEK inhibitor. MEK inhibitors include but are not limited to CI-1040, AZD6244, PD318088, PD98059, PD334581, RDEA119, 6-Methoxy-7-(3-morpholin-4-yl-propoxy)-4-(4-phenoxy-phenylamino)-quinoline-3-carbonitrile or 4-[3-Chloro-4-(1-methyl-1H-imidazol-2-ylsulfanyl)-phenylamino]-6-methoxy-7-(3-morpholin-4-yl-propoxy)-quinoline-3-carbonitrile, Roche compound RG7420, Trametinib, or combinations thereof. In some embodiments, the MEK inhibitor is CI-1040/PD184352 or AZD6244. Other MEK inhibitors are provided herein.

The first inhibitor may be an ERK inhibitor. ERK inhibitors include but are not limited to VTX11e, AEZS-131, PD98059, FR180204, FR148083, or combinations thereof. In some embodiments, the ERK inhibitor is VTX11e. Other ERK inhibitors are provided herein.

It is to be understood that a combination of MAPK pathway inhibitors may be used. In some embodiments, a second inhibitor may be a RAF inhibitor, MEK inhibitor, or ERK inhibitor as provided herein. In some embodiments, the first inhibitor is a RAF inhibitor and the second inhibitor is a MEK inhibitor. In some embodiments, the RAF inhibitor is Dabrafenib and the MEK inhibitor is Trametinib.

Thus, in some embodiments, a combination therapy for cancer is provided, comprising an effective amount of a RAF inhibitor and a MEK inhibitor. The RAF inhibitor may be a pan-RAF inhibitor or it may be a selective RAF inhibitor.

Any of the therapies including combination therapies described herein are suitable for the treatment of a patient manifesting resistance to a MAPK pathway inhibitor such as a RAF inhibitor or a MEK inhibitor or a patient likely to manifest resistance to such inhibitors. The patient may have a cancer characterized by the presence of a B-RAF mutation. The B-RAF mutation may be but is not limited to B-RAFV600E. The cancer may be but is not limited to melanoma.

Pharmaceutical Formulations, Administration and Dosages

Provided herein are pharmaceutical formulations comprising single agents, such as MAPK pathway inhibitors (and/or pharmacologically active metabolites, salts, solvates and racemates thereof).

In other instances, provided herein are pharmaceutical formulations comprising a combination of agents which can be, for example, a combination of two types of agents such as a RAF inhibitor and/or pharmacologically active metabolites, salts, solvates and racemates thereof in combination with a MEK inhibitor and/or pharmacologically active metabolites, salts, solvates and racemates thereof.

Agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, reference to compounds useful in the therapeutic methods of the invention includes both the free base of the compounds, and all pharmaceutically acceptable salts of the compounds. The term "pharmaceutically acceptable salts" includes derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, and nitric; other acceptable inorganic salts include metal salts such as sodium salt, potassium salt, and cesium salt; and alkaline earth metal salts, such as calcium salt and magnesium salt; and combinations comprising one or more of the foregoing salts. In some embodiments, the salt is a hydrochloride salt.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC(CH_2)_n COOH$ where n is 0-4; organic amine salts such as triethylamine salt, pyridine salt, picoline salt, ethanolamine salt, triethanolamine salt, dicyclohexylamine salt, N,N'-dibenzylethylenediamine salt; and amino acid salts such as arginate, aspariginate, and glutamate, and combinations comprising one or more of the foregoing salts.

The agents of the invention are administered in effective amounts. An "effective amount" is an amount sufficient to provide an observable improvement over the baseline clinically observable signs and symptoms of the disorder treated with the combination.

The effective amount may be determined using known methods and will depend upon a variety of factors, including the activity of the agents; the age, body weight, general health, gender and diet of the subject; the time and route of administration; and other medications the subject is taking. Effective amounts may be established using routine testing and procedures that are well known in the art.

A physician or veterinarian having ordinary skill in the art can readily determine and prescribe the effective amount of the pharmaceutical composition required. For example, the physician or veterinarian could start at doses lower than those required to achieve the desired therapeutic effect and gradually increase the dosage until the desired effect is achieved. In general, a suitable daily dose of will be that amount of the compound that is the lowest dose effective to produce a therapeutic effect.

Generally, therapeutically effective doses of the compounds of this invention for a patient will range from about 0.0001 to about 1000 mg per kilogram of body weight per day, more preferably from about 0.01 to about 50 mg per kg per day.

If desired, the effective daily dose of the active compound may be administered as two, three, four, five, six or more sub-doses administered separately at appropriate intervals throughout the day, optionally, in unit dosage forms.

The agents may be administered using a variety of routes of administration known to those skilled in the art. The agents may be administered to humans and other animals orally, parenterally, sublingually, by aerosolization or inhalation spray, rectally, intracisternally, intravaginally, intraperitoneally, bucally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination. Administration may be concurrent or sequential.

The pharmaceutical formulations may additionally comprise a carrier or excipient, stabilizer, flavoring agent, and/or coloring agent. Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono or di glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

The pharmaceutical products can be released in various forms. "Releasable form" is meant to include instant release, immediate-release, controlled-release, and sustained-release forms.

"Instant-release" is meant to include a dosage form designed to ensure rapid dissolution of the active agent by modifying the normal crystal form of the active agent to obtain a more rapid dissolution.

"Immediate-release" is meant to include a conventional or non-modified release form in which greater than or equal to about 50% or more preferably about 75% of the active agents is released within two hours of administration, preferably within one hour of administration.

"Sustained-release" or "extended-release" includes the release of active agents at such a rate that blood (e.g., plasma) levels are maintained within a therapeutic range but below toxic levels for at least about 8 hours, preferably at least about 12 hours, more preferably about 24 hours after administration at steady-state. The term "steady-state" means that a plasma level for a given active agent or combination of active agents, has been achieved and which is maintained with subsequent doses of the active agent(s) at a level which is at or above the minimum effective therapeutic level and is below the minimum toxic plasma level for a given active agent(s).

The pharmaceutical products can be administrated by oral dosage form. "Oral dosage form" is meant to include a unit dosage form prescribed or intended for oral administration. An oral dosage form may or may not comprise a plurality of subunits such as, for example, microcapsules or microtablets, packaged for administration in a single dose.

Compositions for rectal or vaginal administration are preferably suppositories which can be prepared by mixing the compounds of this invention with suitable non irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 microns. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1 to 5 microns. Predominantly in this application means that at least 70% but preferably more than 90% of all generated aerosol particles are within 1 to 5 micron range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDESTREAM nebulizers (Medic Aid Ltd., West Sussex, England), PARI LC and PARI LC STAR jet nebulizers (Pari Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono or multi lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

Screening Methods

The invention provides in another aspect a method for screening one or more candidate agents identify an agent or combination of agents that (a) convert a sensitive signature in a cancer cell or population of cancer cells to a resistant signature, (b) convert a resistant signature in a cancer cell or population of cancer cells to a sensitive signature, (c) maintain a sensitive signature in a cancer cell or population of cancer cells, and/or (d) maintain a sensitive signature in a cancer cell or population of cancer cells in the presence of a MAPK pathway inhibitor.

The agents may be biological (e.g., protein, nucleic acid, etc.) in nature or they may be chemical in nature (e.g., a small molecule, small organic molecule, etc.). They may be present in a library such as a molecular library, a combinatorial library, a chemical library, and the like. It is to be understood that the agent may be of virtually any nature.

The method involves exposing a cell or a cell population (such as cell line or a primary tumor sample) to an agent and measuring expression of one or more R1, R2, S1 and/or S3 markers in the cell or cell population before and after exposure to the agent. In some instances, the method involves continued exposure of the cell or cell population to the agent or exposure of the cell or cell population to one or more MAPK pathway inhibitors. In some instances, the cell or cell population may be maintained in vitro for an extended period of time following which time it is analyzed again for the expression of one or more R1, R2, S1 or S2 markers. In this way, the method can be used to determine whether the agent effects a permanent change on the status of the cell or cell population.

The method may comprise measuring one or more markers as described herein. In some embodiments, the method comprises measuring a first expression level of one or more markers in a cancer cell or population of cancer cells, and measuring a second expression level of one or more markers in a cancer cell or population of cancer cells in the presence of at least one agent, wherein difference between the first and second expression level is used to determine whether the at least one agent (a) converts a sensitive signature in a cancer cell or population of cancer cells to a resistant signature, (b) converts a resistant signature in a cancer cell or population of cancer cells to a sensitive signature, (c) maintains a sensitive signature in a cancer cell or population of cancer cells, and/or (d) maintains a sensitive signature in a cancer cell or population of cancer cells in the presence of a MAPK pathway inhibitor.

In some embodiments, the cell or population of cells comprises a B-RAF mutation. In some embodiments, the B-RAF mutation is V600E. In some embodiments, the cell or population of cells is a melanoma cell or population of such cells such as a melanoma cell line or a melanoma primary tumor sample. It is to be understood that these screening methods may be used to identify agents that might render sensitive cancers other than melanomas.

In some embodiments, the agent is a member of a molecular library. Accordingly, a method of screening may be a high-throughput screen. The molecular library may be, for example, recombinantly produced or chemically produced. Non-limiting examples of molecular libraries include a small molecule library (e.g., a small organic or inorganic molecule library), a chemical library, a peptide library, an siRNA library, an shRNA library, an anti-sense oligonucleotide library, or an open-reading frame library. In general, a molecular library contains from two to $10^{12}$ molecules, and any integer number therebetween. Methods for preparing libraries of molecules and screening such molecules are well known in the art.

In some embodiments, the cancer cell or population of cancer cells is contacted with a MAPK inhibitor as provided herein.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

EXAMPLES

Example 1

The differentially expressed genes of the invention were identified by analyzing gene expression in a panel of cancer samples including cancer cell lines with known sensitivity or resistance to a MAPK pathway inhibitor, PLX4720. Genes whose expression was associated with sensitivity or resistance to MAPK pathway inhibitors in BRAF_V600-mutant melanoma were identified using the Cancer Cell Line Encyclopedia (CCLE) dataset available online at The Broad Institute (Cambridge, Mass.). Robust multi-array average (RMA)-normalized gene expression profiles and IC50 pharmacological sensitivity data (including that for PLX4720) were identified for 22 BRAF_V600-mutant melanomas. First, genes whose expression was well-correlated with sensitivity or resistance were identified based on an expression pattern across cell lines that was strongly correlated (r>0.6, identifying markers of resistance) or anti-correlated (r<−0.6, identifying markers of sensitivity) with the PLX4720 IC50 values for the same cell lines. Next, genes exhibiting a large magnitude of change between sensitive and resistant cell lines from the above list were filtered based on a median difference of >2 (log 2 units) between the sensitive (PLX4720 IC50<1.6 uM) and resistance (PLX4720 IC50≥8 uM) classes. This filtered gene set is provided in Table 1.

Example 2

To validate the putative markers of sensitivity and resistance identified in Example 1, an independent collection of BRAF_V600-mutant patient-derived melanoma short-term cultures were examined (FIG. 1). It was predicted that MAPK-inhibitor resistant short-term cultures would show low expression of markers associated with sensitivity and high expression of markers associated with resistance. Table 1 lists the relative rank (median log fold change) of the pre-specified sensitivity and resistance markers in this new dataset, with 1 being the best predictor (out of 13,321 genes measured) of the indicated state. Expression of some genes was not measured in this collection. Notably, the vast majority of marker genes validated in this independent sample set, indicating their validity.

What is claimed is:
1. A method of treating a subject having cancer comprising measuring in a cancer sample obtained from a subject having cancer
  (1) expression of one or more resistance markers selected from the group consisting of BDNF, KCNMA1, PAPPA, CCDC180, RRAS, CLMP, EPHA2, HRH1, SCG5, aTSPAN5, BEX1, TMEM200A, TGM2, CD163L1, S100A16, IGFBP6, ITGA3, LOC100130938, C12orf75, FBN2, CRIM1, COL6A2, and EFNB2 ("R1 markers"), and
  (2) expression of
    (a) one or more resistance markers selected from the group consisting of DSE, CYR61, CDH13, PODXL, SERPINE1, NRP1, IL1B, BIRC3, AXL, NUAK1, TCF4, COL5A1, NTM, CCL2, IL1A and TPM1 ("R2 markers"), or
    (b) one or more sensitive markers selected from the group consisting of IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A ("S1 markers"), or
    (c) one or more sensitive markers selected from the group consisting of GYG2, TYR, SLC45A2, PLA1A, ST3GAL6, DCT, CITED1, RAB38, TNFRSF14, GALNT3, MREG, GPM6B, RRAGD, CAPN3, MLANA, and MITF ("S2 markers"), and
  identifying the cancer as resistant to a MAPK pathway inhibitor and administering an effective amount of a non-MAPK pathway inhibitor therapy or a combination of a MAPK pathway inhibitor and a second therapeutic agent to the subject having the resistant cancer, wherein the resistant cancer is characterized as having:
(i) one or more of the R1 markers is up-regulated and
(ii) one or more of the R2 markers is up-regulated or
(iii) one or more of the S1 markers is down-regulated or
(iv) one or more of the S2 markers is down-regulated, or
identifying the cancer as sensitive to a MAPK pathway inhibitor and
administering an effective amount of a MAPK pathway inhibitor to the subject having the sensitive cancer, wherein the sensitive cancer is characterized as having:
(i) one or more of the R1 markers is down-regulated and
(ii) one or more of the R2 markers is down-regulated or
(iii) one or more of the S1 markers is up-regulated or
(iv) one or more of the S2 markers is up-regulated.

2. The method of claim 1, wherein the subject is human and/or has been or is being treated with a MAPK pathway inhibitor.

3. The method of claim 1, wherein the cancer is a cancer treated with a MAPK pathway inhibitor and/or is melanoma and/or comprises a BRAF mutation and/or is a melanoma having a BRAF mutation.

4. The method of 3, wherein the BRAF mutation comprises a V600E mutation.

5. The method of claim 1, wherein expression is mRNA expression or protein expression.

6. The method of claim 1, further comprising altering an existing therapy to the subject, wherein the subject presents a resistant phenotype.

7. The method of claim 1, wherein the cancer is identified as resistant to a MAPK pathway inhibitor and the subject having the resistant cancer is administered an effective amount of a non-MAPK pathway inhibitor therapy or a combination of a MAPK pathway inhibitor and a second therapeutic agent, wherein the resistant cancer is characterized as having:
(i) R1 marker CRIM1 is up-regulated and
(ii) S1 marker KCNN2 is down-regulated.

8. The method of claim 1, wherein the cancer is identified as sensitive to a MAPK pathway inhibitor and the subject having the sensitive cancer is administered an effective amount of a MAPK pathway inhibitor, wherein the sensitive cancer is characterized as having:
(i) R1 marker CRIM1 is down-regulated and
(ii) S1 marker KCNN2 is up-regulated.

9. A method of treating a subject having cancer comprising measuring in a cancer sample obtained from a subject having cancer
(1) expression of one or more sensitive markers selected from the group consisting of IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A ("51 markers"), and
(2) expression of
(a) one or more sensitive markers selected from the group consisting of GYG2, TYR, SLC45A2, PLA1A, ST3GAL6, DCT, CITED1, RAB38, TNFRSF14, GALNT3, MREG, GPM6B, RRAGD, CAPN3, MLANA, and MITF ("S2 markers"), or
(b) expression of one or more resistance markers selected from the group consisting of BDNF, KCNMA1, PAPPA, CCDC180, RRAS, CLMP, EPHA2, HRH1, SCG5, TSPAN5, BEX1, TMEM200A, TGM2, CD163L1, S100A16, IGFBP6, ITGA3, LOC100130938, C12orf75, FBN2, CRIM1, COL6A2, and EFNB2 ("R1 markers"), or
(c) one or more resistance markers selected from the group consisting of DSE, CYR61, CDH13, PODXL, SERPINE1, NRP1, IL1B, BIRC3, AXL, NUAK1, TCF4, COL5A1, NTM, CCL2, IL1A and TPM1 ("R2 markers"), and
identifying the cancer as sensitive to a MAPK pathway inhibitor and
administering an effective amount of a MAPK pathway inhibitor to the subject having the sensitive cancer, wherein the sensitive cancer is characterized as having:
(i) one or more of the S1 markers is up-regulated and
(ii) one or more of the S2 markers is up-regulated or
(iii) one or more of the R1 markers is down-regulated or
(iv) one or more of the R2 markers is down-regulated.

10. The method of claim 9, wherein the MAPK pathway inhibitor is a RAF inhibitor, a MEK inhibitor, or an ERK inhibitor.

11. The method of claim 9, wherein the MAPK pathway inhibitor is a first and a second MAPK pathway inhibitor, wherein the first MAPK pathway inhibitor is a RAF inhibitor and the second MAPK pathway inhibitor is a MEK inhibitor.

12. The method of claim 9, wherein the cancer is identified as sensitive to a MAPK pathway inhibitor and the subject having the sensitive cancer is administered an effective amount of a MAPK pathway inhibitor, wherein the sensitive cancer is characterized as having:
(i) S1 marker KCNN2 is up-regulated and
(ii) R1 marker CRIM1 is down-regulated.

13. A method of treating a subject having cancer comprising measuring in a cancer sample obtained from a subject having cancer
(1) expression of two or more resistance markers selected from the group consisting of BDNF, KCNMA1, PAPPA, CCDC180, RRAS, CLMP, EPHA2, HRH1, SCG5, TSPAN5, BEX1, TMEM200A, TGM2, CD163L1, S100A16, IGFBP6, ITGA3, LOC100130938, C12orf75, FBN2, CRIM1, COL6A2, and EFNB2 ("R1 markers"), and/or
(2) expression of two or more sensitive markers selected from the group consisting of IGSF11, FAM167B, MTUS1, GDF15, LINC00518, LRRK2, ID4, CMTM8, KIAA0226L, C11orf96, D4S234E, TBC1D16, TTYH2, LAMA1, PMEL, PROS1, KCNN2, ESRP1, TRIM63, RXRG, PLEKHH1, CPN1, PI15, GNPTAB, and RNF144A ("51 markers"), and
identifying the cancer as resistant to a MAPK pathway inhibitor and
administering an effective amount of a non-MAPK pathway inhibitor therapy or a combination of a MAPK pathway inhibitor and a second therapeutic agent to the subject having the resistant cancer, wherein the resistant cancer is characterized as having:
(i) two or more of the R1 markers are up-regulated, and optionally
(ii) two or more of the S1 markers are down-regulated, or
identifying the cancer as sensitive to a MAPK pathway inhibitor and administering an effective amount of a MAPK pathway inhibitor to the subject having the sensitive cancer, wherein the sensitive cancer is characterized as having:
(i) two or more of the S1 markers are up-regulated, and optionally
(ii) two or more of the R1 markers are down-regulated.

14. The method of claim 13, wherein the cancer is identified as resistant to a MAPK pathway inhibitor and the subject having the resistant cancer is administered an effective amount of a non-MAPK pathway inhibitor therapy or a combination of a MAPK pathway inhibitor and a second therapeutic agent, wherein the resistant cancer is characterized as having:
(i) CRIM1 and another R1 marker are up-regulated, and optionally
(ii) KCNN2 and another S1 marker are down-regulated.

15. The method of claim 13, wherein the cancer is identified as sensitive to a MAPK pathway inhibitor and administering an effective amount of a MAPK pathway inhibitor to the subject having the sensitive cancer, wherein the sensitive cancer is characterized as having:
(i) KCNN2 and another S1 marker are up-regulated, and optionally
(ii) CRIM1 and another R1 marker are down-regulated.

16. A method of treating a subject with cancer comprising
measuring, in a first cancer cell or population of cancer cells obtained from a subject with cancer, a first expression level of (a) one or more R1 markers, and (b) one or more R2 markers, S1 markers, and/or S2 markers;
contacting a second cancer cell or the population of cancer cells with at least one agent, wherein the second cancer cell is from the same population as the first cancer cell, and
measuring, in the second cancer cell or the population of cancer cells in the presence of the at least one agent, a second expression level of (a) one or more R1 markers, and (b) one or more R2 markers, S1 markers, and/or S2 markers; and
identifying the at least one agent as capable of converting a resistant signature in the cancer cell or population of cancer cells to a sensitive signature, and
administering an effective amount of the at least one agent to the subject prior to, during, or after administration of a MAPK inhibitor,
wherein conversion of the resistant signature to the sensitive signature is characterized by:
(i) the second expression level of the one or more of the R1 markers is down-regulated compared to the first expression level of the one or more R1 markers, and
(ii) the second expression level of the one or more of the R2 markers is down-regulated compared to the first expression level of the one or more R2 markers, or
(iii) the second expression level of the one or more of the S1 markers is up-regulated compared to the first expression level of the one or more S1 markers, or
(iv) the second expression level of the one or more of the S2 markers is up-regulated compared to the first expression level of the one or more S2 markers.

17. The method of claim 16, wherein the first expression level is of two or more R1 markers and/or two or more S1 markers; and
the second expression level is of one or more R1 markers and/or two or more S1 markers; and
the at least one agent is identified as capable of converting a resistant signature in the cancer cell or population of cancer cells to a sensitive signature, wherein conversion of the resistant signature to the sensitive signature is characterized by:
(i) the second expression level of the two or more of the S1 markers is up-regulated compared to the first expression level the two or more of the S1 markers, and optionally
(ii) the second expression level of the two or more of the R1 markers is down-regulated compared to the first expression level the two or more of the R1 markers.

18. The method of claim 16, wherein the at least one agent is obtained from a molecular library.

19. The method of claim 16, wherein the cancer cell or population of cancer cells comprises a B-RAF mutation and/or is a melanoma cell or population of melanoma cells.

20. A method of treating a subject with cancer comprising
measuring, in a first cancer cell or population of cancer cells obtained from a subject with cancer, a first expression level of (a) one or more S1 markers, and (b) one or more S2 markers, R1 markers, and/or R2 markers;
contacting a second cancer cell or the population of cancer cells with at least one agent, wherein the second cancer cell is from the same population as the first cancer cell, and
measuring, in the second cancer cell or the population of cancer cells, in the presence of (1) the at least one agent or (2) a MAPK pathway inhibitor and the at least one agent, a second expression level of (a) one or more S1 markers, and (b) one or more S2 markers, R1 markers, and/or R2 markers; and
identifying the at least one agent as capable of converting a resistant signature in the cancer cell or population of cancer cells to a sensitive signature, and
administering an effective amount of the at least one agent to the subject prior to, during, or after administration of a MAPK inhibitor,
wherein conversion of the resistant signature to the sensitive signature is characterized by:
(i) the second expression level of the one or more of the S1 markers is up-regulated compared to the first expression level of the one or more S1 markers, and
(ii) the second expression level of the one or more of the S2 markers is up-regulated compared to the first expression level of the one or more S2 markers, or
(iii) the second expression level of the one or more of the R1 markers is down-regulated compared to the first expression level of the one or more R1 markers, or
(iv) the second expression level of the one or more of the R2 markers is down-regulated compared to the first expression level of the one or more R2 markers.

21. The method of 20, wherein the MAPK pathway inhibitor is a RAF inhibitor, a MEK inhibitor, or an ERK inhibitor.

22. A method of treating a subject with cancer comprising
administering to a subject having cancer an effective amount of an agent capable of converting a resistant signature to a sensitive signature prior to, during, or after administration of a MAPK inhibitor, wherein the agent is identified by a method comprising
measuring, in a first cancer cell or population of cancer cells obtained from the subject, a first expression level of (a) one or more R1 markers, and (b) one or more R2 markers, S1 markers, and/or S2 markers;
contacting a second cancer cell or the population of cancer cells with at least one agent, wherein the second cancer cell is from the same population as the first cancer cell, and measuring, in the second cancer cell or the population of cancer cells in the presence of the at least one agent, a second expression level of (a) one or more R1 markers, and (b) one or more R2 markers, S1 markers, and/or S2 markers; and identifying the agent as capable of converting a resistant signature in the cancer cell or population of cancer cells to a sensitive signature, wherein conversion of the resistant signature to the sensitive signature is characterized by:

(i) the second expression level of the one or more of the R1 markers is down-regulated compared to the first expression level of the one or more R1 markers, and (ii) the second expression level of the one or more of the R2 markers is down-regulated compared to the first expression level of the one or more R2 markers, or (iii) the second expression level of the one or more of the S1 markers is up-regulated compared to the first expression level of the one or more S1 markers, or (iv) the second expression level of the one or more of the S2 markers is up-regulated compared to the first expression level of the one or more S2 markers.

23. A method of treating a subject with cancer comprising administering to a subject having cancer an effective amount of an agent capable of converting a resistant signature to a sensitive signature prior to, during, or after administration of a MAPK inhibitor, wherein the agent is identified by a method comprising measuring, in a first cancer cell or population of cancer cells obtained from the subject, a first expression level of (a) one or more S1 markers, and (b) one or more S2 markers, R1 markers, and/or R2 markers;

contacting a second cancer cell or the population of cancer cells with at least one agent, wherein the second cancer cell is from the same population as the first cancer cell, and measuring, in the second cancer cell or the population of cancer cells, in the presence of (1) the at least one agent or (2) a MAPK pathway inhibitor and the at least one agent, a second expression level of (a) one or more S1 markers, and (b) one or more S2 markers, R1 markers, and/or R2 markers; and identifying the agent as capable of converting a resistant signature in the cancer cell or population of cancer cells to a sensitive signature, wherein conversion of the resistant signature to the sensitive signature is characterized by:

(i) the second expression level of the one or more of the S1 markers is up-regulated compared to the first expression level of the one or more S1 markers, and (ii) the second expression level of the one or more of the S2 markers is up-regulated compared to the first expression level of the one or more S2 markers, or (iii) the second expression level of the one or more of the R1 markers is down-regulated compared to the first expression level of the one or more R1 markers, or (iv) the second expression level of the one or more of the R2 markers is down-regulated compared to the first expression level of the one or more R2 markers.

* * * * *

UNITED STATES PATENT AND TRADEMARK OFFICE
CERTIFICATE OF CORRECTION

PATENT NO. : 10,968,484 B2
APPLICATION NO. : 14/774909
DATED : April 6, 2021
INVENTOR(S) : Cory M. Johannessen et al.

It is certified that error appears in the above-identified patent and that said Letters Patent is hereby corrected as shown below:

On the Title Page

Item (57), ABSTRACT Line 1:
"The invention provides methods and devices for determining molecular signatures in a cancer that predict response to a MARPK pathway inhibitor and methods of use of such signatures."

Should read:
--The invention provides methods and devices for determining molecular signatures in a cancer that predict response to a MAPK pathway inhibitor and methods of use of such signatures.--

In the Drawings

In Figure 1:
Please add --FIG. 1--

In the Specification

At Column 1, under the section titled "CROSS-REFERENCE TO RELATED APPLICATIONS":
"This application claims the benefit of the filing date of U.S. Provisional Application No. 61/800,304, filed Mar. 15, 2013, the entire contents of which are incorporated by reference herein."

Should read:
--This application is a national stage filing under 35 U.S.C. §371 of International Application No. PCT/US2014/023927, filed March 12, 2014, which was published under PCT Article 21(2) in English, and which claims the benefit of the filing date of U.S. Provisional Application No. 61/800,304, filed March 15, 2013, the entire contents of both of which are incorporated by reference herein.--

In the Claims

Signed and Sealed this
Twenty-ninth Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,968,484 B2

At Column 38, Line 43:
"PAPPA, CCDCI80, RRAS, CLMP, EPHA2, HRH1,"

Should read:
--PAPPA, CCDC80, RRAS, CLMP, EPHA2, HRH1,--

At Column 38, Line 44:
"SCG5, aTSPAN5, BEX1, TMEM200A, TGM2,"

Should read:
--SCG5, TSPAN5, BEX1, TMEM200A, TGM2,--

At Column 39, Line 61:
"and RNF144A ("51 markers"), and"

Should read:
--and RNF144A ("S1 markers"), and--

At Column 40, Line 3:
"KCNMA1, PAPPA, CCDCI80, RRAS, CLMP,"

Should read:
--KCNMA1, PAPPA, CCDC80, RRAS, CLMP,--

At Column 40, Line 44:
"PAPPA, CCDCI80, RRAS, CLMP, EPHA2, HRH1,"

Should read:
--PAPPA, CCDC80, RRAS, CLMP, EPHA2, HRH1,--

At Column 40, Line 55:
"and RNF144A ("51 markers"), and"

Should read:
--and RNF144A ("S1 markers"), and--